(12) United States Patent
Burnett

(10) Patent No.: US 11,197,774 B2
(45) Date of Patent: *Dec. 14, 2021

(54) DEVICES AND METHODS FOR GASTROINTESTINAL STIMULATION

(71) Applicant: BAROnova, Inc., San Carlos, CA (US)

(72) Inventor: Daniel R. Burnett, San Francisco, CA (US)

(73) Assignee: BAROnova, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/590,865

(22) Filed: May 9, 2017

(65) Prior Publication Data

US 2017/0246018 A1   Aug. 31, 2017

Related U.S. Application Data

(63) Continuation of application No. 11/702,840, filed on Feb. 5, 2007, now Pat. No. 9,700,450, which is a
(Continued)

(51) Int. Cl.
*A61F 5/00* (2006.01)
*A61N 1/05* (2006.01)
(Continued)

(52) U.S. Cl.
CPC ............ *A61F 5/0079* (2013.01); *A61F 5/003* (2013.01); *A61F 5/0036* (2013.01); *A61F 5/0089* (2013.01); *A61N 1/0509* (2013.01); *A61N 1/36007* (2013.01); *A61F 2210/0014* (2013.01); *A61N 1/0472* (2013.01); *A61N 1/0507* (2013.01)

(58) Field of Classification Search
None
See application file for complete search history.

(56) References Cited

U.S. PATENT DOCUMENTS 2,499,045 A   2/1950   Ray et al.
3,154,077 A   10/1964  Cannon
(Continued)

FOREIGN PATENT DOCUMENTS

DE   4012642      10/1991
JP   2010-537790  12/2010
(Continued)

OTHER PUBLICATIONS

U.S. Appl. No. 10/671,191, filed Sep. 24, 2003.
(Continued)

*Primary Examiner* — Jennifer Pitrak McDonald
*Assistant Examiner* — Elizabeth K So
(74) *Attorney, Agent, or Firm* — Levine Bagade Han LLP

(57) ABSTRACT

An intragastric weight-loss device is disclosed. The device includes a proximal occlusion member comprising a spiral structure, a bridging member, and a distal occlusion member. The spiral structure can be configured to spiral into a bulbous shape when the proximal occlusion member is delivered into the stomach. The bridging member can extend from the proximal occlusion member. The distal occlusion member can be coupled to a distal end of the bridging member. The proximal occlusion member can be configured to intermittently obstruct a pyloric valve of a patient such that passage of food through the pyloric valve is slowed.

14 Claims, 23 Drawing Sheets

Related U.S. Application Data continuation-in-part of application No. 10/915,716, filed on Aug. 9, 2004, now Pat. No. 9,498,366, which is a continuation-in-part of application No. 10/833,950, filed on Apr. 27, 2004, now Pat. No. 8,048,169, which is a continuation-in-part of application No. 10/671,191, filed on Sep. 24, 2003, now Pat. No. 6,994,095.

(60) Provisional application No. 60/764,673, filed on Feb. 3, 2006, provisional application No. 60/525,105, filed on Nov. 26, 2003, provisional application No. 60/490,421, filed on Jul. 28, 2003.

(51) Int. Cl.
  *A61N 1/36* (2006.01)
  *A61N 1/04* (2006.01)

(56) References Cited

U.S. PATENT DOCUMENTS

| | | |
|---|---|---|
| 3,915,171 A | 10/1975 | Shermeta |
| 4,133,315 A | 1/1979 | Berman et al. |
| 4,240,412 A | 12/1980 | James |
| 4,246,893 A | 1/1981 | Berson |
| 4,311,146 A | 1/1982 | Wonder |
| 4,315,509 A | 2/1982 | Smit |
| 4,341,218 A | 7/1982 | U |
| 4,368,739 A | 1/1983 | Nelson |
| 4,416,267 A | 11/1983 | Garren et al. |
| 4,485,805 A | 12/1984 | Foster, Jr. |
| 4,517,979 A | 5/1985 | Pecenka |
| 4,598,699 A | 7/1986 | Garren et al. |
| 4,648,383 A | 3/1987 | Angelchik |
| 4,657,020 A | 4/1987 | Lifton |
| 4,694,827 A | 9/1987 | Weiner et al. |
| 4,735,214 A | 4/1988 | Berman |
| 4,762,128 A | 8/1988 | Rosenbluth |
| 4,836,204 A | 8/1989 | Landymore et al. |
| 4,878,905 A | 11/1989 | Blass |
| 4,925,446 A | 5/1990 | Garay et al. |
| 4,930,496 A | 6/1990 | Bosley |
| 4,946,440 A | 8/1990 | Hall |
| 5,011,488 A | 4/1991 | Ginsburg |
| 5,047,065 A | 9/1991 | Vogel et al. |
| 5,108,420 A | 4/1992 | Marks |
| 5,129,915 A | 7/1992 | Cantenys |
| 5,192,301 A | 3/1993 | Kamiya et al. |
| 5,234,454 A | 8/1993 | Bangs |
| 5,246,445 A | 9/1993 | Yachia et al. |
| 5,282,829 A | 2/1994 | Hermes |
| 5,306,300 A | 4/1994 | Berry |
| 5,312,343 A | 5/1994 | Krog et al. |
| 5,423,872 A | 6/1995 | Cigaina |
| 5,509,888 A | 4/1996 | Miller |
| 5,514,091 A | 5/1996 | Yoon |
| 5,514,178 A | 5/1996 | Torchio |
| 5,540,701 A | 7/1996 | Sharkey et al. |
| 5,545,210 A | 8/1996 | Hess et al. |
| 5,634,936 A | 6/1997 | Linden et al. |
| 5,674,192 A | 10/1997 | Sahatjian et al. |
| 5,676,688 A | 10/1997 | Jaker et al. |
| 5,707,355 A | 1/1998 | Zimmon |
| 5,750,585 A | 5/1998 | Park et al. |
| 5,752,971 A | 5/1998 | Rosenbluth et al. |
| 5,782,800 A | 7/1998 | Yoon |
| 5,820,584 A | 10/1998 | Crabb |
| 5,853,422 A | 12/1998 | Huebsch et al. |
| 5,947,991 A | 9/1999 | Cowan |
| 5,976,174 A | 11/1999 | Ruiz |
| 6,067,991 A | 5/2000 | Forsell |
| 6,102,928 A | 8/2000 | Bonutti |
| 6,112,703 A | 9/2000 | Handelsman |
| 6,117,159 A | 9/2000 | Huebsch et al. |
| 6,152,144 A | 11/2000 | Lesh et al. |
| 6,159,219 A | 12/2000 | Ren |
| 6,162,201 A | 12/2000 | Cohen |
| 6,183,520 B1 | 2/2001 | Pintauro et al. |
| 6,245,090 B1 | 6/2001 | Gilson et al. |
| 6,270,515 B1 | 8/2001 | Linden et al. |
| 6,371,974 B1 | 4/2002 | Brenneman et al. |
| 6,409,656 B1 | 6/2002 | Sangouard et al. |
| 6,454,785 B2 | 9/2002 | De Hoyos Garza |
| 6,488,962 B1 | 12/2002 | Berner et al. |
| 6,503,264 B1 | 1/2003 | Birk |
| 6,527,701 B1 | 3/2003 | Sayet et al. |
| 6,527,739 B1 | 3/2003 | Bigus et al. |
| 6,540,789 B1 | 4/2003 | Silverman et al. |
| 6,544,291 B2 | 4/2003 | Taylor |
| 6,558,400 B2 | 5/2003 | Deem et al. |
| 6,579,301 B1 | 6/2003 | Bales et al. |
| 6,600,953 B2 | 7/2003 | Flesler et al. |
| 6,652,578 B2 | 11/2003 | Bailey et al. |
| 6,675,809 B2 | 1/2004 | Stack et al. |
| 6,689,046 B2 | 2/2004 | Sayet et al. |
| 6,702,846 B2 | 3/2004 | Mikus |
| 6,740,121 B2 | 5/2004 | Geitz |
| 6,755,869 B2 | 6/2004 | Geitz |
| 6,802,868 B2 | 10/2004 | Silverman et al. |
| 6,860,895 B1 | 3/2005 | Akerfeldt et al. |
| 6,994,095 B2 | 2/2006 | Burnett |
| 7,011,621 B2 | 3/2006 | Sayet et al. |
| 7,037,344 B2 | 5/2006 | Kagan et al. |
| 7,054,690 B2 | 5/2006 | Imran et al. |
| 7,087,072 B2 | 8/2006 | Marino et al. |
| 7,120,498 B2 | 10/2006 | Imran et al. |
| 7,121,283 B2 | 10/2006 | Stack et al. |
| 7,122,058 B2 | 10/2006 | Levine et al. |
| 7,146,984 B2 | 12/2006 | Stack et al. |
| 7,160,312 B2 | 1/2007 | Saadat |
| 7,167,750 B2 | 1/2007 | Knudson et al. |
| 7,186,251 B2 | 3/2007 | Malecki et al. |
| 7,291,160 B2 | 11/2007 | DeLegge |
| 7,320,696 B2 | 1/2008 | Gazi et al. |
| 7,588,584 B2 | 9/2009 | Fogarty et al. |
| 7,842,053 B2 | 11/2010 | Chanduszko et al. |
| 8,048,169 B2 | 11/2011 | Burnett et al. |
| 8,257,389 B2 | 9/2012 | Chanduszko et al. |
| 9,924,948 B2 | 3/2018 | Burnett et al. |
| 9,931,122 B2 | 4/2018 | Burnett et al. |
| 10,166,133 B2 | 1/2019 | Burnett et al. |
| 2002/0010481 A1 | 1/2002 | Jayaraman |
| 2002/0013601 A1 | 1/2002 | Nobles et al. |
| 2002/0038100 A1 | 3/2002 | Okada |
| 2002/0091395 A1 | 7/2002 | Gabbay |
| 2002/0161341 A1 | 10/2002 | Stinson et al. |
| 2002/0165589 A1 | 11/2002 | Imran et al. |
| 2002/0188354 A1 | 12/2002 | Peghini |
| 2002/0198470 A1 | 12/2002 | Imran et al. |
| 2002/0198479 A1 | 12/2002 | Talish |
| 2003/0023150 A1 | 1/2003 | Yokoi et al. |
| 2003/0040804 A1 | 2/2003 | Stack et al. |
| 2003/0078611 A1 | 4/2003 | Hashiba et al. |
| 2003/0093117 A1 | 5/2003 | Saadat |
| 2003/0109931 A1 | 6/2003 | Geltz |
| 2003/0109935 A1 | 6/2003 | Geitz |
| 2003/0120328 A1 | 6/2003 | Jenkins et al. |
| 2003/0144708 A1 | 7/2003 | Starkebaum |
| 2003/0152601 A1 | 8/2003 | Kanayama |
| 2003/0153806 A1 | 8/2003 | Miller |
| 2003/0158601 A1 | 8/2003 | Silverman et al. |
| 2004/0034408 A1 | 2/2004 | Majercack |
| 2004/0059368 A1 | 3/2004 | Maryanka |
| 2004/0107004 A1 | 6/2004 | Levine et al. |
| 2004/0117031 A1 | 6/2004 | Stack et al. |
| 2004/0158331 A1 | 8/2004 | Stack et al. |
| 2004/0172141 A1 | 9/2004 | Stack et al. |
| 2004/0172142 A1 | 9/2004 | Stack et al. |
| 2004/0213825 A1 | 10/2004 | Levy |
| 2004/0230222 A1 | 11/2004 | van der Burg et al. |
| 2004/0236357 A1 | 11/2004 | Kraemer et al. |
| 2004/0267378 A1 | 12/2004 | Gazi et al. |
| 2005/0033331 A1 | 2/2005 | Burnett et al. |

(56) References Cited

U.S. PATENT DOCUMENTS

| | | |
|---|---|---|
| 2005/0033332 A1 | 2/2005 | Burnett |
| 2005/0038460 A1 | 2/2005 | Jayaraman |
| 2005/0038470 A1 | 2/2005 | van der Burg et al. |
| 2005/0055039 A1 | 3/2005 | Burnett et al. |
| 2005/0064009 A1 | 3/2005 | Bates |
| 2005/0090873 A1 | 4/2005 | Imran et al. |
| 2005/0096673 A1 | 5/2005 | Stack et al. |
| 2005/0149142 A1 | 7/2005 | Starkebaum |
| 2005/0192627 A1 | 9/2005 | Whisenant et al. |
| 2005/0192629 A1 | 9/2005 | Saadat et al. |
| 2005/0251154 A1 | 11/2005 | Chanduszko et al. |
| 2005/0273060 A1 | 12/2005 | Levy et al. |
| 2005/0288786 A1 | 12/2005 | Chanduszko |
| 2006/0020278 A1 | 1/2006 | Burnett et al. |
| 2006/0178691 A1 | 8/2006 | Binmoeller |
| 2006/0217763 A1 | 9/2006 | Abbott et al. |
| 2006/0259074 A1 | 11/2006 | Kelleher et al. |
| 2006/0282107 A1 | 12/2006 | Hashiba et al. |
| 2006/0293742 A1 | 12/2006 | Dann et al. |
| 2007/0016262 A1 | 1/2007 | Gross et al. |
| 2007/0027548 A1 | 2/2007 | Levine et al. |
| 2007/0056591 A1 | 3/2007 | McSwain |
| 2007/0083224 A1 | 4/2007 | Hively |
| 2007/0135831 A1 | 6/2007 | Burnett et al. |
| 2007/0178160 A1 | 8/2007 | Burnett |
| 2007/0198082 A1 | 8/2007 | Kapadia et al. |
| 2007/0239284 A1 | 10/2007 | Skerven et al. |
| 2007/0250132 A1 | 10/2007 | Burnett |
| 2009/0118757 A1 | 5/2009 | Burnett et al. |
| 2009/0118758 A1 | 5/2009 | Burnett et al. |
| 2009/0177288 A1 | 7/2009 | Wallsten |
| 2009/0182357 A1 | 7/2009 | Burnett et al. |
| 2009/0182358 A1 | 7/2009 | Burnett et al. |
| 2009/0187200 A1 | 7/2009 | Burnett et al. |
| 2009/0187201 A1 | 7/2009 | Burnett et al. |
| 2009/0198210 A1 | 8/2009 | Burnett et al. |
| 2009/0216262 A1 | 8/2009 | Burnett et al. |
| 2009/0299486 A1 | 12/2009 | Shohat et al. |

FOREIGN PATENT DOCUMENTS

| | | |
|---|---|---|
| WO | WO 1988/00027 | 1/1988 |
| WO | WO 1990/00369 | 1/1990 |
| WO | WO 2000/048672 | 8/2000 |
| WO | WO 2002/091961 | 11/2002 |
| WO | WO 2003/017882 | 3/2003 |
| WO | WO 2005/009288 | 2/2005 |
| WO | WO 2005/104989 | 10/2005 |
| WO | WO 2006/020370 | 2/2006 |
| WO | WO 2006/135857 | 12/2006 |
| WO | WO 2007/027812 | 3/2007 |
| WO | WO 2007/092390 | 8/2007 |
| WO | WO 2007/092501 | 8/2007 |
| WO | WO 2009/033049 | 3/2009 |

OTHER PUBLICATIONS

U.S. Appl. No. 10/833,950, filed Apr. 27, 2004.
U.S. Appl. No. 10/915,716, filed Aug. 9, 2004.
U.S. Appl. No. 11/215,430, filed Aug. 29, 2005.
U.S. Appl. No. 11/602,620, filed Nov. 20, 2006.
U.S. Appl. No. 11/702,840, filed Feb. 5, 2007.
U.S. Appl. No. 11/702,888, filed Feb. 5, 2007.
U.S. Appl. No. 12/351,705, filed Jan. 9, 2009.
U.S. Appl. No. 12/351,686, filed Jan. 9, 2009.
U.S. Appl. No. 12/351,665, filed Jan. 9, 2009.
U.S. Appl. No. 12/351,644, filed Jan. 9, 2009.
U.S. Appl. No. 12/434,594, filed May 1, 2009.
U.S. Appl. No. 14/618,868, filed Feb. 10, 2015.
U.S. Appl. No. 12/205,403, filed Sep. 5, 2008.
U.S. Appl. No. 12/352,497, filed Jan. 12, 2009.
U.S. Appl. No. 12/352,508, filed Jan. 12, 2009.
U.S. Appl. No. 14/495,371, filed Sep. 24, 2014.
U.S. Appl. No. 15/356,188, filed Nov. 18, 2016.
U.S. Appl. No. 14/849,450, filed Sep. 9, 2015.

DEVICES AND METHODS FOR GASTROINTESTINAL STIMULATION

CROSS-REFERENCE TO RELATED APPLICATIONS

This application is a continuation of U.S. patent application Ser. No. 11/702,840, filed Feb. 5, 2007, which claims priority to U.S. Provisional Patent Application No. 60/764,673 filed Feb. 3, 2006 and which is a continuation-in-part of U.S. patent application Ser. No. 10/915,716, filed on Aug. 9, 2004 (now U.S. Pat. No. 9,498,366 issued Nov. 22, 2016), which is a continuation-in-part of Ser. No. 10/833,950, filed Apr. 27, 2004 (now U.S. Pat. No. 8,048,169 issued Nov. 1, 2011), which claims priority to U.S. Provisional Patent Application No. 60/525,105, filed Nov. 26, 2003 and which is a continuation-in-part of U.S. patent application Ser. No. 10/671,191, filed Sep. 24, 2003 (now U.S. Pat. No. 6,994,095 issued Feb. 7, 2006), which claims priority to U.S. Provisional Patent Application No. 60/490,421, filed Jul. 28, 2003, the contents of each of which are incorporated herein by reference in its entirety.

BACKGROUND OF THE INVENTION

1. Field of the Invention

The present invention relates generally to medical devices and methods. More specifically, the invention relates to devices and methods that for treating the gastrointestinal tract.

2. Description of the Related Art

Obesity has become a medical problem of epidemic proportions in the United States. Recent governmental studies estimate that as many as 40% of Americans are obese (defined as a Body Mass Index over 30), and of those, almost 20% are morbidly obese. Unfortunately, there is no indication that these percentages will decrease and every indication that they will increase in the coming years.

Studies have linked obesity to countless health risks, a small sampling of which includes cardiovascular disease, cancer, diabetes, orthopedic injuries and complaints, obstructive sleep apnea, chronic fatigue and depression. Despite billions of dollars spent searching for obesity cures, conducting research into nutrition and exercise, and educating the public about obesity, efforts to date have been largely ineffective.

Many Americans have tried combating obesity with diet, exercise and even medications, to no avail. Most people who lose weight through diet and exercise gain it back again in a short period of time. Available medications can have serious side effects, as was evidenced by the recent scare with the Fen-Phen dietary medication. Faced with the difficulty of diet and exercise, nutritional information that seems to change radically and rapidly, and diet medications and supplements that typically do not work and may cause serious side effects, many obese people become frustrated and either decide to remain obese or choose to pursue a more drastic treatment option.

The more drastic options typically involve surgical procedures, such as stomach stapling, other gastric reduction surgical techniques, placement of a constrictive band around the outside of the stomach, and gastric bypass. The most well-known procedure, in part due to well-publicized experiences of celebrities like Al Roker and Carney Wilson, is the gastric bypass operation, known technically as a Roux-En-Y gastric bypass. In this procedure, the stomach is actually bypassed, and a very small stomach-like pouch remains, making a patient feel full after ingesting a small amount of food. Although gastric bypass can be highly effective, it is acknowledged to be a very, high-risk operation, with a 1-2% mortality rate, a number of possible complications such as digestive problems, and a recovery period of up to 6 months. The other surgical alternatives are also associated with either high risk, low rate of effectiveness, or both.

Stemming from the high risks of gastric surgical procedures and the ineffectiveness of diet and exercise for many obese people, a number of medical devices have been developed to address weight loss and obesity, but these too have numerous drawbacks. Some devices, for example, try to bypass a portion of the stomach or small intestine by essentially creating a tube or chute through which food passes without any nutrients or calories being absorbed. Such devices are described, for example, in U.S. Pat. Nos. 5,820,584, 6,675,809, and 6,740,121. Other techniques involve placing space-occupying balloons and other devices within the stomach to make the patient feel full after eating small amounts of food. One such a device, for example, is described in U.S. Pat. No. 6,755,869.

One significant drawback of currently available devices such as absorption-reducing gastrointestinal sleeves, gastric electrical stimulators and space occupying gastric balloons is that they are directly attached to the wall of the gastrointestinal tract. Such direct attachment may often lead to erosion and ulceration of the lining of the stomach or small intestine. Another significant risk with currently available devices is that if the direct attachment to gastrointestinal tissue fails for some reason, the device may pass through the pyloric valve of the stomach and into the small intestine. From there, the device may cause a blockage in the small or large intestine, which typically requires surgery and may be fatal if discovered too late.

Another approach for obesity treatment, as described, for example, in U.S. Pat. No. 7,160,312, involves performing a minimally invasive surgical procedure on a stomach, typically to reduce its volume. Yet another approach involves severing or stimulating the vagus nerve in an attempt to slow the rate at which food passes from the stomach into the duodenum. Others have tried slowing gastric emptying by placing implants or injecting bulking agents into tissue at or immediately adjacent the pyloric valve. Such techniques are described, for example, in U.S. Pat. Nos. 6,540,789 and 6,802,868 and U.S. Patent Application Publication No. 2003/0153806. In general, all of these types of therapies require invasive, sometimes irreversible, surgical procedures, risking a number of potential serious side effects to the functioning of the gastrointestinal tract.

Of course, obesity is not the only health problem associated with the gastrointestinal tract. It is offered here merely as an example of one serious gastrointestinal-related health problem without an ideal means of treatment or cure. Many other health conditions are caused or directly related to functioning of the gastrointestinal tract, and like obesity, many such conditions do not currently have optimal medical or surgical treatments.

Therefore, a need exists for effective, minimally invasive or non-invasive devices and methods for obesity and other conditions related to the gastrointestinal tract. Ideally, such devices and methods would be relatively easy to use and deploy in a patient and would help treat obesity and/or other conditions without a high risk of side effects or severe complications. Ideally, such devices and methods would also be reversible and/or capable of being modified via external devices or minimally invasive means. Also ideally, the device will build, and improve, upon the safety and efficacy data demonstrated by previous obesity therapies, such as the Transnemonix gastric stimulator. At least some of these objectives will be met by the present invention.

SUMMARY

The present invention provides devices, methods, and systems for gastric stimulation of a patient. Generally, the stimulation devices include a body for anchoring the device in the gastrointestinal tract and at least one stimulation member, which may be one or more energy delivery members, one or more sensors, or a combination of both.

The body maintains the device within the gastric space and prevents passage of the device through the pyloric valve. Preferably, the body is configured to be disposed within the pyloric portion of the patient's stomach. The body is preferably configured so that it is not rigidly anchored or affixed to the stomach wall tissue, thus avoiding erosion and ulceration of the stomach wall.

In one aspect of the present invention, a device for treating a portion of a gastrointestinal tract of a patient includes a body and at least one stimulation member coupled with the body. The body is adapted to maintain at least part of the device within a pyloric portion of the patient's stomach and to intermittently engage, without directly attaching to, stomach tissue. The stimulation member(s) are adapted for performing one or more functions in the patient's gastrointestinal tract, such as energy delivery or controlling the flow of the stomach contents out of the stomach.

In some embodiments, the body comprises an expandable body that forms a stomach retention portion having sufficient size and rigidity to prevent passage of the expandable body through a pyloric valve out of the stomach. In one embodiment, the stimulation member is an energy delivery member coupled with the stomach retention portion. The expandable body is expandable from a first, contracted configuration for delivery through an esophagus of the patient to a second, expanded configuration for preventing passage of the stomach retention portion through the pyloric valve. Alternatively, the device may be non-expandable and thus adapted to be placed into the stomach via an incision in a wall of the stomach. In a number of embodiments, the body further includes a tissue engagement portion adapted to intermittently engage pyloric stomach tissue without causing significant damage to the tissue. In some embodiments, some or all of the stimulation member(s) are coupled with the tissue engagement portion. Such a tissue engagement portion, for example, may comprise at least one compliant material.

In some embodiments, the body further comprises a bridging member, such as a pyloric valve spanning member, extending from the expandable body at least partially through a pyloric valve of the patient. Optionally, some or all of the stimulation member(s) may be coupled with the bridging member.

Optionally, the body may further include a distal expandable member coupled with the bridging member and adapted to reside in a duodenum of the patient. One or more energy delivery members may optionally be coupled with either the bridging member or the distal anchor member. In some embodiments, for example, the energy delivery member is coupled with the distal expandable member and is adapted to extend into a small intestine of the patient. The distal anchor member itself may be sufficiently small to pass through the pyloric valve through natural peristalsis but sufficiently large to resist passing back into the stomach. Alternatively, the distal anchor member may be sufficiently large so as to require placement into the duodenum beyond the pyloric valve.

In some embodiments, the stomach retaining portion, the pyloric valve spanning member and/or the distal expandable member may be adapted to change configurations while residing in the gastrointestinal tract. For example, in some embodiments, the pyloric valve spanning member is adapted to change its length and/or its diameter. Such configuration changes may be triggered by receipt and processing of one or more signals by a receiver and processor of the device. Alternatively, configuration changes may be triggered upon sensing a environmental condition.

In various embodiments, any of a number of energy delivery members, sensors and/or additional components may be coupled with the body for performing various functions in the gastrointestinal tract.

Some embodiments of the device also include attachment means for attaching to a catheter device extended into the stomach to implant, adjust or modify the device. For example, attachment means may include a magnetically active material, a conductive metal, a hook or any other suitable attachment device. Such attachment means allow a device to be modified, adjusted, recharged and/or the like via a catheter placed through tube placed into the stomach via an oropharyngeal tube or a nasogastric tube, thus obviating the need for removal of the device to make adjustments.

Some embodiments may further include at least one receiver for receiving signals from one or more transmitters located outside the patient or implanted in the patient. Such embodiments may optionally include a processor adapted to process the received signals and provide the processed data to the at least one energy delivery member. Some embodiments further include a rechargeable power source adapted to be recharged via an external charging device. Other embodiments include an intermittently placed nasogastric or orogastric charging device. In other embodiments, any other suitable devices or combinations may be coupled with the anchoring member to facilitate or enhance the performance of a function in the gastrointestinal tract.

In yet another aspect of the present invention, a method for performing a function in a gastrointestinal tract of a patient involves delivering stimulation device into the stomach and performing a function in the gastrointestinal tract using at least one stimulation member coupled with the body of the stimulation device. The anchoring device itself may have any of the features described above. In an embodiment, delivering the stimulation device involves advancing the anchoring device through an esophagus of the patient in a first, contracted configuration, and releasing the stimulation device to allow at least a portion of the device to expand from the first, contracted configuration to a second expanded configuration. The portion of the stimulation device in the expanded second configuration is adapted to prevent passage of the stimulation device through a pyloric valve of the patient. Alternatively, delivering the stimulation device may involve passing the device through an incision in a wall of the patient's stomach.

In various embodiments, performing the function in the gastrointestinal tract may involve, but is not limited to, transmitting energy, stimulating gastrointestinal tissue to evoke a response, intermittently obstructing the pylorus and/or transmitting data, storing data and/or the like. In some embodiments, the method further involves sensing at least one patient characteristic, or environmental condition, using at least one sensing device coupled with the stimulation device.

In some embodiments, the method may also include transmitting data to the stimulation device via at least one transmitter and receiving the transmitted data via a receiver coupled with the stimulation device. Such transmitting may be performed via one or more transmitters located outside the patient, implanted in the patient or a combination of both. Some embodiments also include processing the transmitted data via a processor coupled with the anchoring member. Optionally, the method may also include recharging the energy delivery member while the gastrointestinal device remains within the patient. In one embodiment, recharging the energy delivery member is performed via an external charging device located outside the patient. Alternatively, recharging the energy delivery member may be performed via a catheter device passed into the patient's stomach via the patient's esophagus. In one embodiment, recharging the energy delivery member involves recharging the battery of the gastrointestinal device. The method may optionally also involve recharging a power source coupled with the anchoring member.

In some embodiments, the stimulation device is adapted to intermittently obstruct the pyloric valve of the patient's gastrointestinal tract, thus slowing the passage of food through the valve. In addition to the intermittent obstruction of the pylorus, the body of the stimulation device may incorporate electrodes for transmitting energy to adjacent tissues. This combination therapy may provide synergistic benefit from the reduction in the rate of gastric emptying combined with the benefits or electrical, or other energy, stimulation.

In another aspect of the invention, a method for sensing one or more patient characteristic, or environmental condition, in a gastrointestinal tract of a patient involves delivering a stimulation device into the stomach and sensing one or more patient characteristics in the gastrointestinal tract using at least one sensing device included in the stimulation device. Such a method may further include performing a function in the gastrointestinal tract using one or more energy delivery members included in the stimulation device. Various embodiments of the method may include any of the features described above, with the preferred embodiment involving the activation of energy transmission device once said sensors have been triggered.

In an alternative embodiment, the device of the present invention may be anchored within the duodenum using a similar interference fit design. This embodiment capitalizes on the transition of the duodenum from a large region dubbed the "duodenal bulb" into the smaller lumen of the "proximal duodenum". In this embodiment, the stomach anchoring element and pylorus spanning element are replaced by the duodenal bulb anchoring element and the duodenal transition spanning element. The distal anchoring element is replaced by the proximal duodenum anchoring element, which may be as simple as a segment of tubing.

These and other aspects and embodiments of the invention are described in greater detail below, with reference to the attached drawing figures.

BRIEF DESCRIPTION OF THE SEVERAL VIEWS OF THE DRAWINGS

The accompanying drawings, which are incorporated herein and form a part of the specification, illustrate the present invention and, together with the description, further serve to explain the principles of the invention and to enable a person skilled in the pertinent art to make and use the invention.

DETAILED DESCRIPTION

The stimulation device of the present invention provides a mechanism that allows control of flow of materials through a pyloric valve and/or application of energy to portions of the gastrointestinal tract. The embodiments described below may be expandable between a contracted delivery configuration and an expanded, implanted configuration to ease implantation and/or removal. However it should be appreciated that embodiments may be adapted for placement via a surgical procedure involving an incision in the stomach wall, and thus the invention is not limited to an expanding device delivered through the esophagus. Thus, the description that follows is provided primarily for exemplary purposes, and no one embodiment should be interpreted to limit the scope of the invention as a whole.

Figure 1:
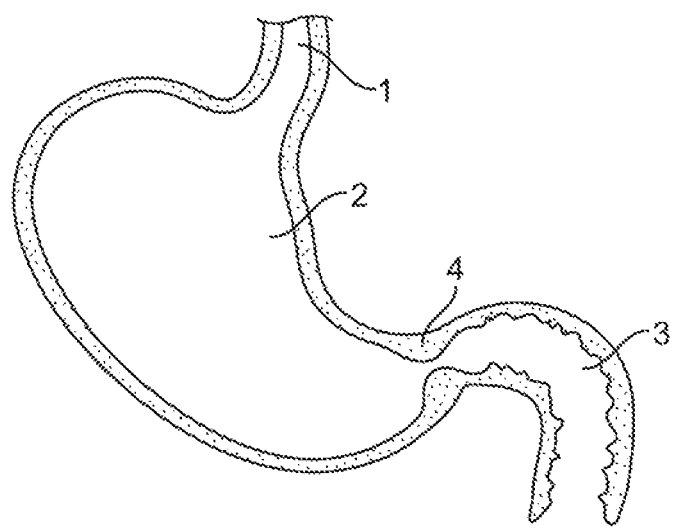
FIG. 1 is a cross-sectional view of the anatomy of the upper gastrointestinal tract.

Referring first to FIG. 1, an upper portion of the gastrointestinal tract includes the esophagus 1 that is in fluid communication with a proximal end of the stomach 2, and a duodenum 3 that is in fluid communication with a distal end of the stomach 2. Fluid communication between the stomach 2 and duodenum 3 is regulated by a pyloric valve 4, which is a sphincter muscle that contracts and expands. Generally, the stomach 2 defines a gastric portion, the pyloric valve defines a pyloric portion and the duodenum defines an upper, or superior, portion of an intestinal portion of the gastrointestinal tract.

Figure 2A:
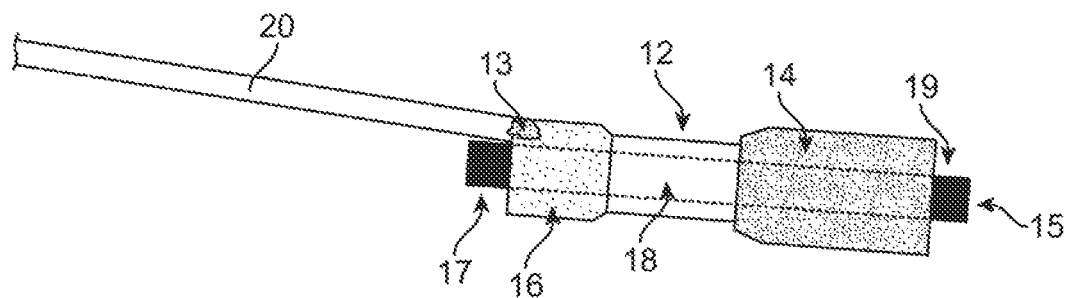
FIGS. 2A-2C are side views of an embodiment of a stimulation device in a contracted, partially expanded, and fully expanded configuration, respectively.
Figure 2B:
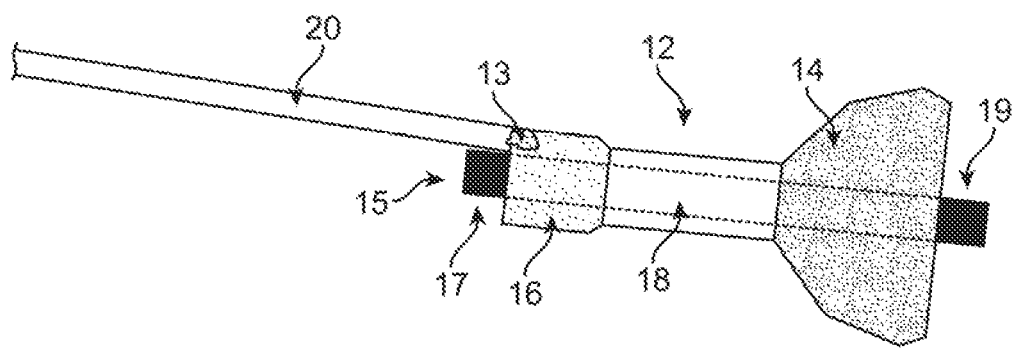
Figure 2C:
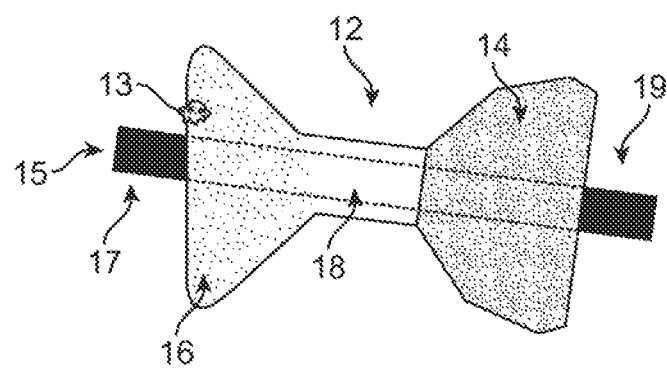

Now referring to FIGS. 2A-2C an embodiment of a gastrointestinal stimulation device will be described. Stimulation device 10 generally includes a pylorus spanning element, such as bridging member 12, that extends between distal occlusion member 14 and proximal occlusion member 16, and stimulation member 18. Bridging member 12 and occlusion members 14 and 16 combine to form the structural body 11 of stimulation device 10. Body 11 may also be referred to herein as an anchoring body because it is generally configured to anchor, or locate, stimulation device 10 in a desired position within the gastrointestinal tract.

Portions of body 11 may be selectively expanded. For example, FIG. 2A illustrates the contracted delivery configuration of stimulation device 10. FIG. 2B illustrates a partially expanded configuration of stimulation device 10 in which distal occlusion member 14 is expanded and proximal occlusion member 16 is contracted. In both FIGS. 2A and 2B, the stimulation device is shown coupled to a catheter 20 that may be used for delivery and inflation or expansion of the occlusion members. Finally, FIG. 2C illustrates stimulation device 10 in a fully expanded configuration.

Bridging member 12 is a generally elongate cylindrical member that defines the space between occlusion members 14, 16. The length of bridging member 12 is selected so that an occlusion member 14, 16 is positioned on each side of the pyloric valve after implantation. In particular, bridging member 12 is sized so that first occlusion member 14 is located within the superior pan of the duodenum, i.e., distal of the pyloric valve, and so that occlusion member 16 is located within the pyloric canal of the stomach, i.e., proximal of the pyloric valve. Stimulation device 10 may be configured with a relatively shortened bridging member 12 to inhibit the relative movement of stimulation device relative to the pyloric valve.

The outer diameter of bridging member 12 is selected so that it provides a desired amount of obstruction in the pyloric valve. If it is desired to provide minimal obstruction the outer diameter of bridging member 12 may be, for example, 5 mm or less. If, however, significant obstruction of the opening in the pyloric valve is desired an outer diameter greater than 5 mm and up to 10 mm, but preferably 8-10 mm, may be selected. It should however, be appreciated that the outer diameter and shape of bridging member 12 may be selected to provide the desired obstruction in the pyloric valve of a particular patient. For example, bridging member 12 may include channels to allow some flow of materials from the stomach past the pyloric valve.

Each of occlusion members 14, 16 is configured to be expandable between a contracted configuration and an expanded configuration. The contracted configuration is generally utilized during implantation and removal procedures to reduce the overall size of device 10. The expanded configuration is utilized to maintain device 10 in place. In the present embodiment, occlusion members 14 and 16 are generally conical. In particular, distal occlusion member 14 is configured so that its outer diameter increases at locations further distal from bridging member 12. Proximal occlusion member 16 is oriented so that its outer diameter increases at locations further proximal from bridging member 12. As a result, the largest diameter portion of occlusion member 14 is located nearest the distal end of device 10 and the largest diameter portion of occlusion member 16 is located nearest the proximal end of device 10. The outer diameter of each of occlusion members 14 and 16 nearest bridging member 12 is generally the same as the outer diameter of bridging member 12 so that there is a smooth transition between occlusion members 14 and 16 and bridging member 12. It should be appreciated that the size of the occlusion members may be selected as desired. As shown, one occlusion member may be larger than the other. Alternatively, the occlusion members may be the same size.

One or both of occlusion members 14 and 16 may be an expandable scaffold. Such a scaffold may be made of a shape memory alloy or super-elastic alloy, such as Nitinol. The scaffold may be compressed into a contracted configuration and then expanded into the desired expanded configuration by self-expansion or by supplying an activation energy, e.g., electrical, heat, RF energy, etc. Alternatively, an expandable foam may be used to provide the expandable body.

As a further alternative, one or both of occlusion members 14 and 16 may be an inflatable body. The inflatable body may be a balloon that is inflatable by injecting an inflation medium through infusion port 13. The inflation medium may be any biocompatible fluid such as, for example, saline.

Any suitable materials may be used to form any embodiments of the devices described. In one embodiment, for example, the device may comprise an expandable balloon fabricated from silicone, silicone elastomers, latex, polyurethane, PTFE, FEP, and/or the like. Alternatively, self-expanding materials, such as foam or hydrogels, which typically expand upon contact with fluids, may be utilized within the device. If such self-expanding materials are utilized, they may be disposed in the device, and a fluid such as saline may be infused to expand the materials.

Generally, the proximal portion of the stimulation device body, e.g., proximal occlusion member 16 of body 11, has a supportive or structural function, for assuring that the device has a large enough cross-sectional diameter to prevent passage of the device through the pyloric valve. Typically, the distal portion, e.g., bridging member 12 and distal occlusion member 14 of body 11, functions to contact the pyloric valve and/or tissue adjacent the pyloric valve, to intermittently and/or partially block the valve or provide stimulation and to stabilize the position of the stimulation device in a desired location. It should be appreciated that such a configuration allows the stimulation device to be located without requiring it to be directly anchored in the gastrointestinal tract.

In some embodiments, the distal portion is made of compliant material, so that when it contacts stomach tissue in, around or adjacent the pyloric valve, it does not harm the tissue. In some embodiments, the proximal portion and distal portion are made of the same material, with the proximal portion having a greater amount of material, greater wall thickness or the like, relative to the distal portion.

An erodible or biodegradable material may cover occlusion members 14, 16. Such a covering may be included over one or both of the occlusion members and may be configured to temporarily constrain occlusion members 14, 16 in a contracted state. After the device has been ingested or placed within the stomach, contact with the surrounding fluids may naturally erode the covering thus allowing the covered occlusion member to expand or inflate. Materials configured to erode at differing rates or in different environments, if desired may cover the occlusion members.

In the present embodiment, stimulation member 18 is disposed on bridging member 12. The stimulation member 18 may be one or more energy delivery member, one or more sensors, or a combination of both. Such energy delivery members and sensors may be coupled with any portion of stimulation device 10, such as any portions residing in the stomach, spanning the pyloric valve or disposed within the duodenum. Stimulation member 18 includes an energy delivery member and stimulation member 18 is disposed on bridging member 12. It should be appreciated, however, that in some embodiments, a stimulation device may include one or more energy delivery members or sensors coupled with another portion of the stimulation device via one or more tethers.

In the present embodiment, the energy delivery member includes at least one electrode that is configured to apply energy to gastrointestinal tissue. For example, the energy delivery member may be configured to deliver types of energy such as, but not limited to, radiofrequency, ultrasound, microwave, cryogenic, laser, electrical, mechanical or thermal energy.

It should be appreciated that another type of stimulation member that may be used in stimulation device 10 in addition to or as an alternative to the energy delivery member is a substance delivery member. For example, stimulation member 18 may include a therapeutic substance, or substances, that is releasably coupled. Exemplary substances include, but are not limited to lipids, drugs, enzymes, diagnostic agents, lipids, vitamins, minerals or the like. Such substances may be releasably coupled with an outer surface of the stimulation device, contained in a degradable or erodable coating, or may be housed within one or more refillable reservoirs.

Another type of stimulation member 18 that may be used on stimulation device 10 is a space-occupying member for occupying space in the stomach to enhance the patient's feeling of satiety. Yet another example of a stimulation member is a trigger adapted to elicit a biological response, such as a surface coating adapted to induce a satiety response. Any suitable imaging device may be another type of stimulation member. Generally, any suitable device for performing a function within the gastrointestinal tract may be considered a stimulation member.

In a still further example, the stimulation member may include at least one sensor coupled with the body of the stimulation device for sensing one or more characteristics in the gastrointestinal tract. Such a sensor (or sensors) may be adapted to sense, for example, pH, temperature, bile content, nutrient content, fats, sugars, alcohol, opiates, drugs, analytes, electrolytes and/or hemoglobin.

A processor and circuitry (not shown) may also be employed that is adapted to process data related to the sensed signals and to provide the processed data to at least one energy delivery member. These or other embodiments may also include a receiver for receiving transmitted data from a remote source, a transmitter for transmitting data, a data storage module, a rechargeable power source, or any suitable combination thereof. Additionally, an energy transmitter may be incorporated into the device to provide a source for energy applied by an energy delivery member. The energy transmitter may include a processor and circuitry for relaying information as well. As a further alternative, the stimulation member may be configured to focus energy applied from outside the body of the patient at a desired location, for example, through inductive coupling.

Stimulation device 10 may include an optional lumen 15 defined by body 11 that extends through stimulation device 10. Lumen 15 is configured to partially and/or intermittently obstruct a gastric opening in a contracted, partially expanded, and fully expanded configuration, respectively. Optional lumen 15 may allow for the passage of fluids and food through stimulation device 10 entering the lumen 15 through entry port 17 and exiting through lumen exit port 19. Lumen 15 may be designed to allow for the passage of a reduced volume of food through stimulation device 10.

Lumen 15 may be configured so that it is capable of actively pumping or metering the flow of contents of the stomach into the intestine through stimulation device 10. The pump or valve may be configured to simply open and allow for the passage of the stomach contents through lumen 15 upon sensing the presence of foreign objects, such as food, in the stomach or upon sensing a predetermined pressure from the contents. Other sensing parameters may include temperature and/or pH levels. Alternatively, the pump or valve may be configured to actively pump the stomach contents through lumen 15 via a pumping mechanism that may be automatically activated or manually activated by the patient or physician through wireless communication. The valve may be configured as a unidirectional valve to allow the flow of fluids and food only from the stomach to the intestinal tract.

Figure 3A:
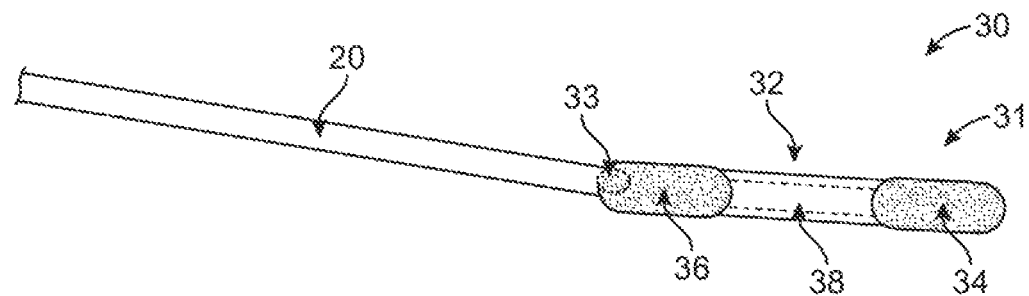
FIGS. 3A-3C are side views of another embodiment of a stimulation device in a contracted, partially expanded, and fully expanded configuration, respectively.
Figure 3B:
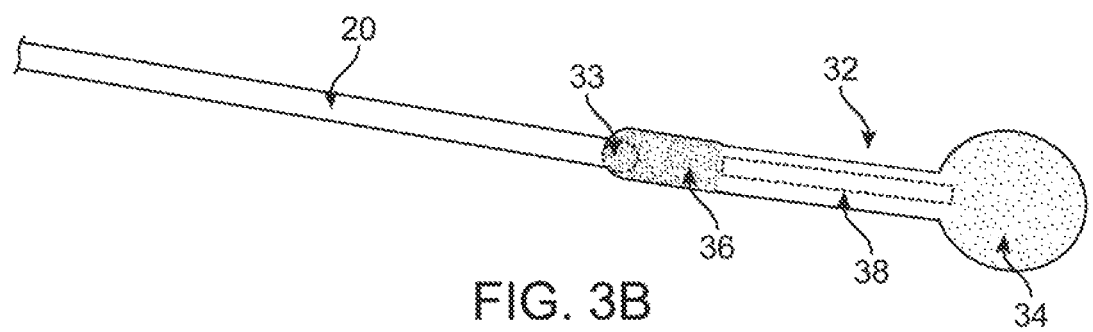
Figure 3C:
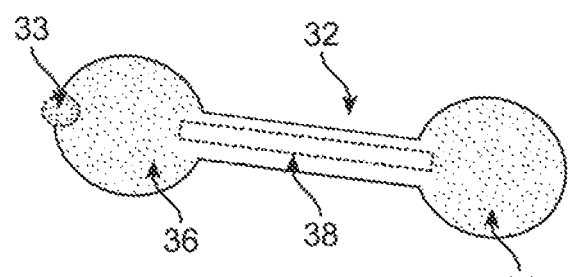

Referring to FIGS. 3A-3C another embodiment, stimulation device 30, will be described. The stimulation device 30 generally includes bridging member 32 that extends between a first, distal occlusion member 34 and a second, proximal occlusion member 36, and stimulation member 38. Stimulation member 38 is disposed on bridging member 32, similar to the previously described embodiments and may include one or more energy delivery members, one or more sensors, any other type of stimulation member or combinations thereof.

As shown in the figures, portions of body 31 may be selectively expanded. For example, FIG. 3A illustrates the contracted delivery configuration of stimulation device 30. FIG. 3B illustrates a partially expanded configuration of stimulation device in which distal occlusion member 34 is expanded and proximal occlusion member 36 is contracted. In both FIGS. 3A and 3B, stimulation device is shown coupled to a catheter 20 that may be used for delivery and/or inflation of the occlusion members through infusion port 33. Finally, FIG. 3C illustrates stimulation device 30 in a fully expanded configuration.

Stimulation device 30 may optionally also include a lumen extending through body 31 that provides a passageway for substances from the stomach to the duodenum. It should be appreciated that the lumen may include a pump and/or valve as described with respect to the previous embodiments.

Bridging member 32 and occlusion members 34 and 36 combine to form the structural body 31 of stimulation device 30. In the present embodiment, occlusion members 34 and 36 are spherical and bridging member 32 is cylindrical. Furthermore, proximal occlusion member 36 is larger than distal occlusion member 34. It should be appreciated that the occlusion members may have the same or different shapes and they may be the same or different sizes.

Figure 4A:
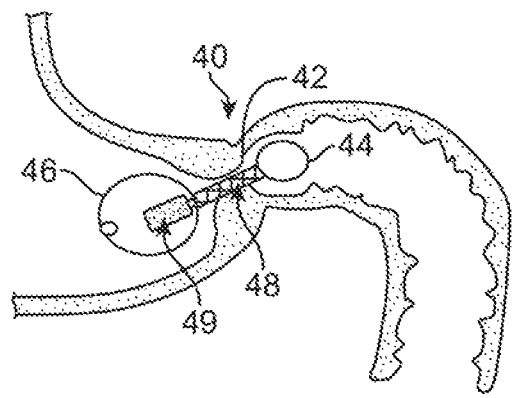
FIGS. 4A-4C are side views of various embodiments of a stimulation device.
Figure 4B:
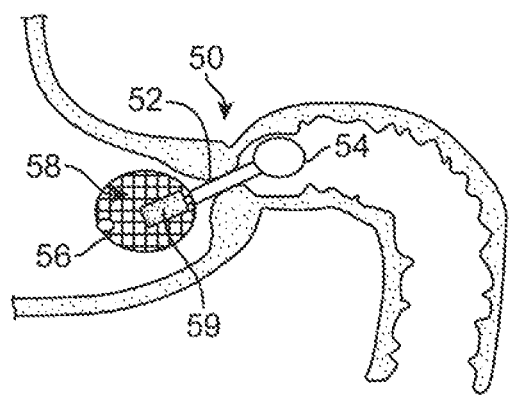
Figure 4C:
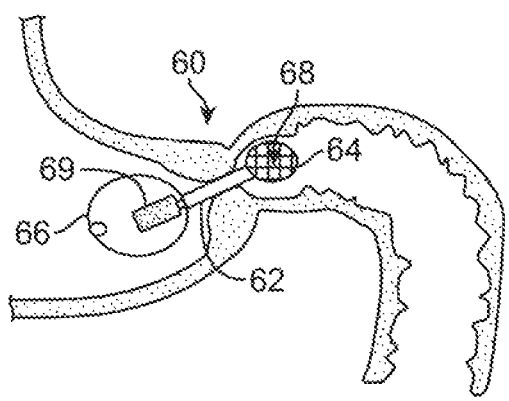

Referring to FIGS. 4A-4C various embodiments will of the stimulation device will be described. In the embodiments illustrated in these figures the configuration of the body of the stimulation device is generally identical to body 31 of stimulation device 30 described above. As a result, the detailed description of that structure will not be repeated. It should, however, be appreciated that the design of the structural bodies illustrated are not limited to the structure of body 31, but any of the body structures described herein may be employed. As shown in FIG. 4A, stimulation device 40 generally includes a pair of occlusion members 44 and 46, bridging member 42, and stimulation member 48. Stimulation member 48 is disposed on bridging member 42 so that stimulation member 48 may directly interface the tissue of the pyloric valve. Stimulation device 40 also includes energy transmitter 49 that is configured to selectively transmit energy to stimulation member 48.

Energy transmitter 49 may be disposed on any desired portion of stimulation device 40. As shown, energy transmitter is disposed on occlusion member 46. It should also be appreciated that energy transmitter may be configured to generate energy based on internal or external controls. The energy transmitter may include circuitry and/or a battery so that it may generate an energy output.

In another embodiment, the stimulation device 50 generally includes a pair of occlusion members 54 and 56, bridging member 52, stimulation member 58 and energy transmitter 59, as shown in FIG. 4B. In the present embodiment, stimulation member 58 is disposed on occlusion member 56 and energy transmitter 59 is disposed on occlusion member 56. Because stimulation member 58 is disposed on occlusion member 56, it may be used to more easily apply stimulation directly to the tissue of the gastric antrum, proximal of the pyloric valve.

Stimulation device 60 is shown in FIG. 4C. The stimulation device 60 generally includes a pair of occlusion members 64 and 66, bridging member 62, stimulation member 68 and energy transmitter 69, as shown in FIG. 4B. In the present embodiment, stimulation member 68 is disposed on occlusion member 64 and energy transmitter 69 is disposed on occlusion member 66. Because stimulation member 68 is disposed on occlusion member 64, it may be used to more easily apply stimulation directly to the tissue of the proximal duodenum.

Figure 5A:
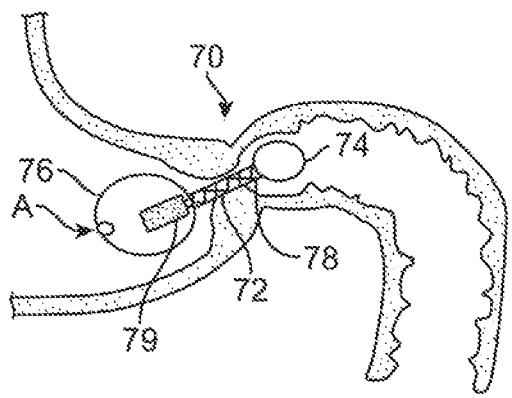
FIGS. 5A-5C are side views of various embodiments of a stimulation device illustrating triggering events for sensors of the devices.
Figure 5B:
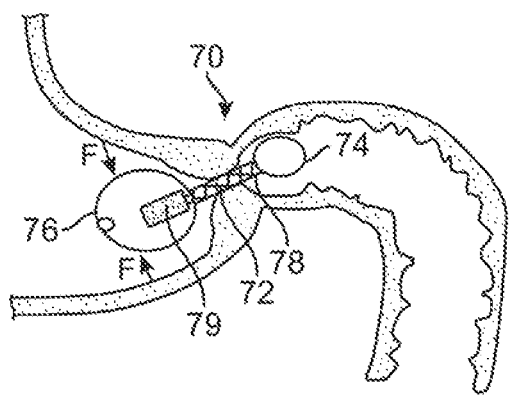
Figure 5C:
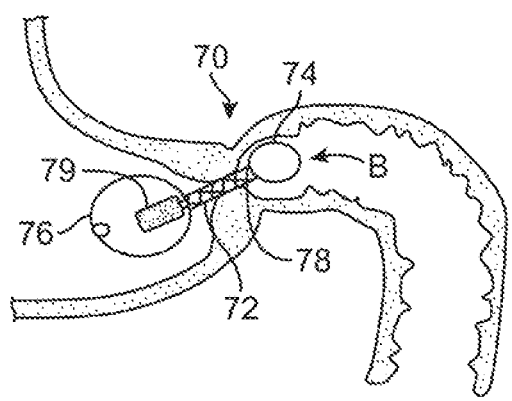

The stimulation members incorporated into any of the embodiments of the stimulation device described herein may be triggered automatically or manually and they may be triggered internally by conditions of the environment adjacent the device or by external controllers. FIGS. 5A-5C illustrate embodiments of a stimulation device, which are structurally similar to stimulation device 40 described above, that are configured to be triggered responsive to environmental conditions. As shown, stimulation device 70 includes a pair of occlusion members 74 and 76, bridging member 72, stimulation member 78 and energy transmitter 79.

In these embodiments, sensors may be placed on any portion of the device (gastric, pyloric or intestinal), and may sense one of many environmental conditions in order to trigger operation of the device. For example, one or more sensors may be disposed within, on or adjacent occlusion member 76 and configured to sense environmental conditions (shown as stimulus A) as pH, temperature, salinity, specific foods and/or specific compounds as shown in FIG. 5A. The sensing of those conditions may be used to control the transmission of energy into surrounding tissues via stimulation member 78. Alternatively, and as shown in FIG. 5B, one or more sensors may be disposed within, on or adjacent occlusion member 76 and configured to sense force and/or pressure (shown as stimulus F). As a further example, one or more sensors may be disposed within, on or adjacent distal occlusion member 74 and may be configured to sense any desired condition, such as pH, temperature, salinity, specific foods, specific compounds, force and/or pressure (shown as stimulus B). As with all of the aforementioned embodiments and all to follow, the device is capable of internal or external charging and is capable of internal or external programming to control its function.

Figure 6:
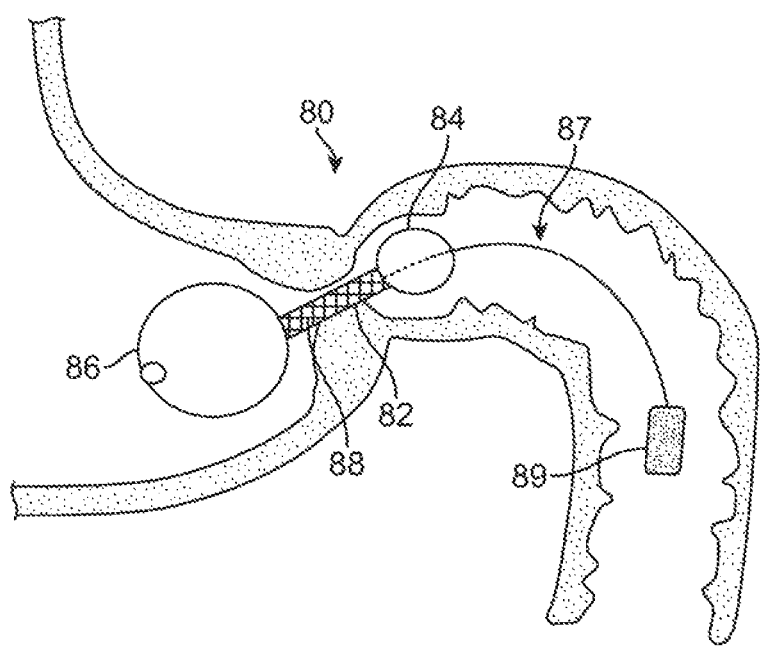
FIG. 6 is a side view of another embodiment of a stimulation device.

Referring to FIG. 6, another embodiment of the stimulation device will be described. Stimulation device 80 generally includes a body 81 constructed from a pair of occlusion members 84 and 86 and bridging member 82, stimulation member 88 and energy transmitter 89. Energy transmitter 89 is coupled to body 81 by tether 87 such that energy transmitter 89 is spaced from body 81. It should be appreciated that tether 87 may be constructed so that energy transmitter is spaced from body 81 in any direction. For example, tether 87 may be configured so that energy transmitter 89 is spaced from body 81 so that it is distal of body 81 toward the intestines (as shown) or so that it is proximal of body 81.

FIGS. 7A-7E illustrate alternative embodiments for shape-memory or locking body designs. Each of these designs can be expanded and compressed to fit within a delivery pod and then regain the expanded shape once in the stomach either through shape-memory properties or via endoscopic manipulation. Each of the embodiments of the stimulation device 90 generically includes a body 91 that is constructed with distal occlusion member 94, proximal occlusion member 96 and bridging member 92. The primary difference between the embodiments is the structure of proximal occlusion member 96 each of which includes shell 93 and core 95. Generally, core 95 is configured so that it may transition between a contracted delivery configuration and an expanded configuration. Expansion of core 95 causes shell 93 to increase in diameter, thereby increasing the overall size of proximal occlusion member 96.

Figure 7A:
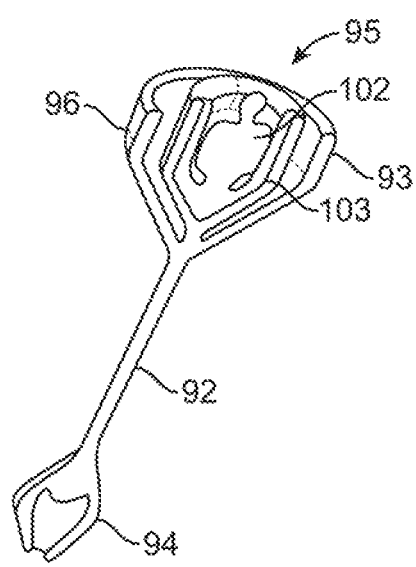
FIGS. 7A-7E are perspective, side and cross-sectional views of various embodiments of a stimulation device.

In the embodiment shown in FIG. 7A, core 95 includes a generally cylindrical plug 102 that is coupled to a generally annular flexible wall. Translation of plug 102 along the longitudinal axis of the stimulation device 90 causes flexible wall 103 to invert and core 95 to expand radially outward. Radial expansion of flexible wall 103 causes shell 93 to expand radially outward.

Figure 7B:
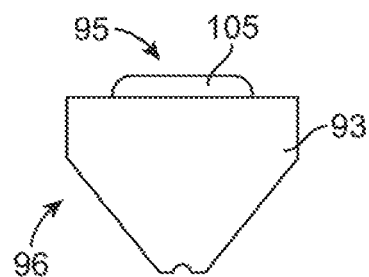
Figure 7C:
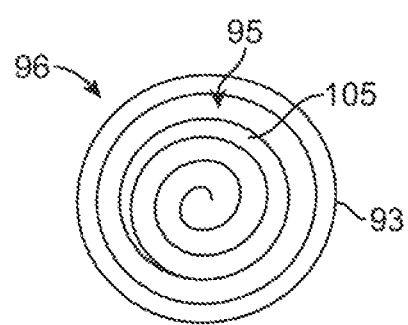
Figure 7D:
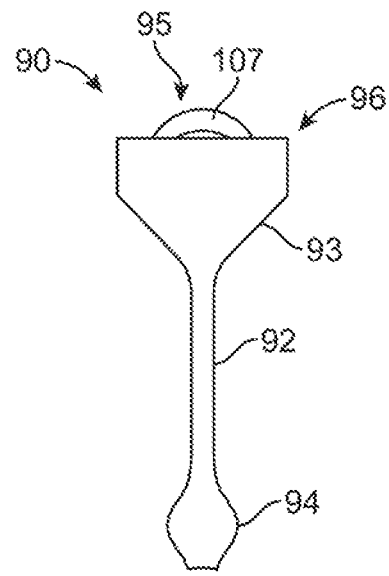

In another embodiment, shown in FIGS. 7B and 7C, core 95 includes an elongate band 105 that is configured to be rolled about an axis parallel to the longitudinal axis of stimulation device 90 to form a horizontal roll plug. As elongate band 105 is rolled, the diameter of the rolled band increases which causes shell 93 to extend radially outward. Similarly, FIG. 7D illustrates another rolling plug embodiment. However, elongate band 107 is configured to be rolled about an axis perpendicular to the longitudinal axis of stimulation device 90 thereby forming a vertical roll plug. Rolling elongate band 107 increases its effective outer diameter which forces shell 93 to expand radially outward. Locking features may be included so that bands 105 and 107 may be locked in the rolled configuration, if desired.

Figure 7E:
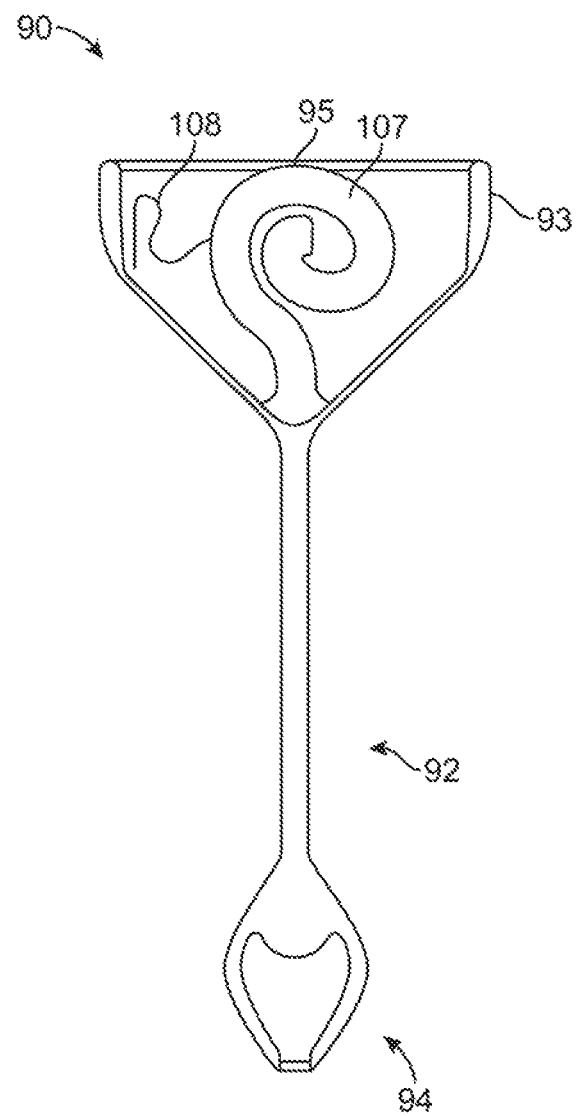

Additionally, a tether may be included that extends between core 95 and shell 93 to ease contraction of occlusion member 96. FIG. 7E illustrates a stimulation device with a vertical roll plug that includes an S-shaped tether 108 connecting elongate band 107 with shell 93. Tether 108 ensures that shell 93 reduces in diameter, e.g., by folding asymmetrically, during extraction of stimulation device 90 so that the device may be easily removed through the esophagus.

Figure 8A:
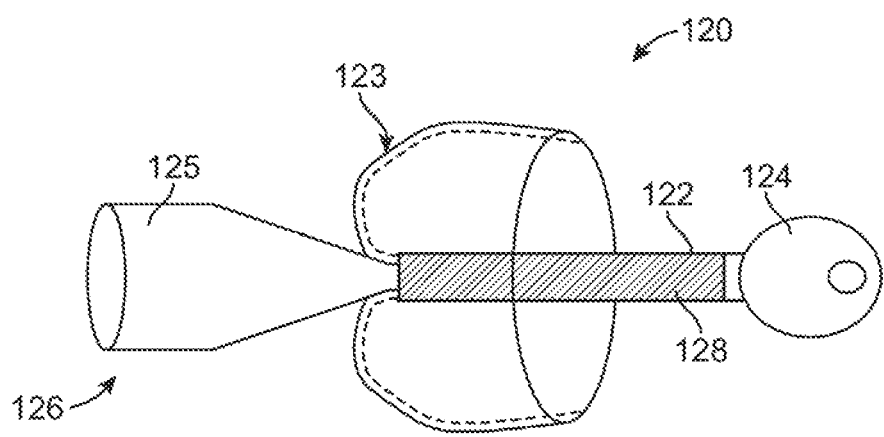
FIGS. 8A and 8B are side views of another embodiment of a stimulation device.
Figure 8B:
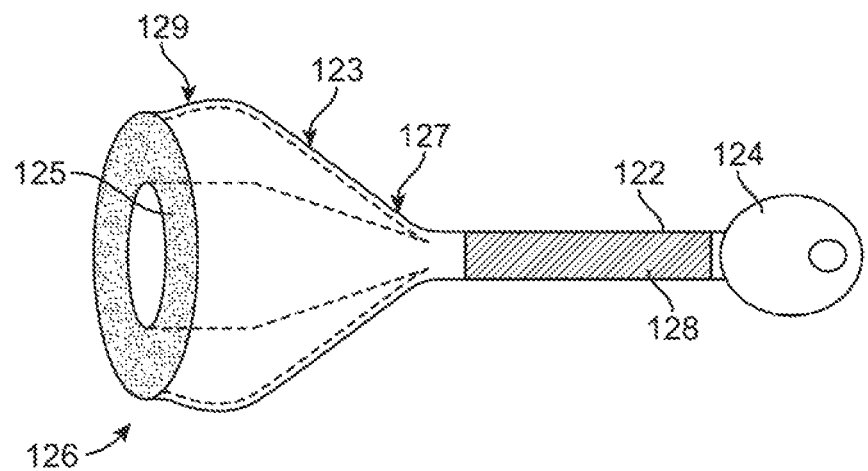

FIGS. 8A-8B illustrate stimulation device 120 that is configured to be of inserted and inverted in order to achieve the gastric retention. Stimulation device 120 includes body 121 that is constructed from distal occlusion member 124, proximal occlusion member 126 and bridging member 122, stimulation member 128 and an energy transmitter (not shown). As with the previously described embodiments, bridging member 122 extends between occlusion member 124 and 126 and is configured to be located within the pyloric valve. Stimulation member 128 is disposed within, on or adjacent bridging member 122, but it should be appreciated that it may be located within, on or adjacent any portion of body 121.

In the present embodiment, proximal occlusion member 126 of the stimulation device 120 includes an invertible shell 123 and core 125. Shell 123 includes a tissue contacting/engaging portion 127 and a support portion 129. Generally, support portion 129 is more rigid/stiffer than tissue contact portion 127, so that the former helps maintain the cross-sectional diameter of the device 120 so that it cannot pass through the pyloric valve, while the latter is more compliant so that it can contact stomach tissue allowing for a good electrical contact without causing significant damage.

The various components of the device 120 may be constructed of any suitable materials, such as those already described or any other suitable materials now known or hereafter discovered. In one embodiment, core 125 is a solid material, such as silicone, but in other embodiments, core 125 may be hollow. Core 125 may have any suitable size, shape, cross-sectional diameter or the like. In one embodiment, core 125 a cross-sectional diameter of between about 5 mm and about 30 mm, and preferably about 10 mm.

Shell 123 may be made of the same or different material as core 125, and also may have any suitable size, shape, cross-sectional diameter or the like. In an embodiment, support portion 129 of the shell 123 is thicker than tissue contact portion 127. In other embodiments, support portion 129 may be made of a different material than tissue contact portion 127.

Bridging member 122 may be an extension of core 125, shell 123 or both, or may instead be a separate piece coupled with core 125 and/or shell 123. Bridging member 122 may have any suitable length and diameter to allow it to pass through the pyloric valve. In one embodiment, its cross-sectional diameter is about 1.0 cm or less and its length is about 3.0 cm or greater.

Distal occlusion member 124 may also have any suitable size, shape, or configuration, with some embodiments being expandable, some being self-expanding, and others configured to not expand at all. In an embodiment, occlusion member 124 has a greatest cross-sectional diameter of about 30 mm or smaller, and preferably about 25 mm or smaller, and even more preferably about 21 mm or smaller.

One or both of occlusion members 124 and 126 may include a hole 131 or a surface feature which may have any configuration for allowing coupling of an energy delivery member or another device with the respective occlusion member for delivering, adjusting and/or retrieving stimulation device 120. Occlusion members 124 and 126 may be made of any suitable material.

Although not drawn to scale, FIG. 8A illustrates the collapsed or inverted state of stimulation device 120. In this configuration, shell 123 is compressed to a smaller cross-sectional diameter for delivery, such as through a delivery tube or catheter. After device 120 is delivered to the stomach, shell 123 is inverted to its expanded state, as shown in FIG. 8B, and stimulation device 120 may then act to intermittently obstruct the pyloric valve and/or apply energy to the surrounding tissue.

Figure 9A:
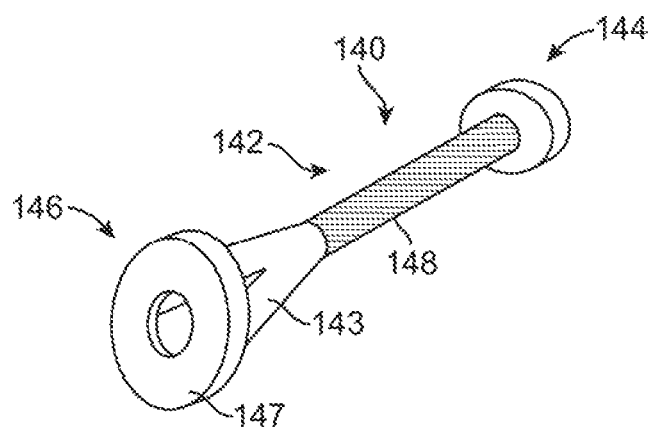
FIGS. 9A-9C are perspective and side views of various embodiments of a stimulation device.
Figure 9B:
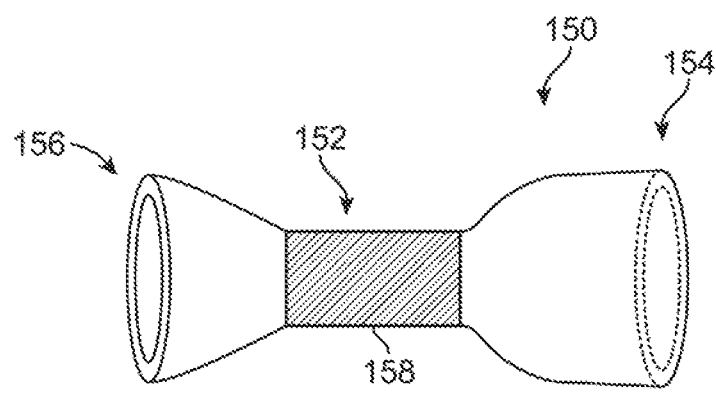
Figure 9C:
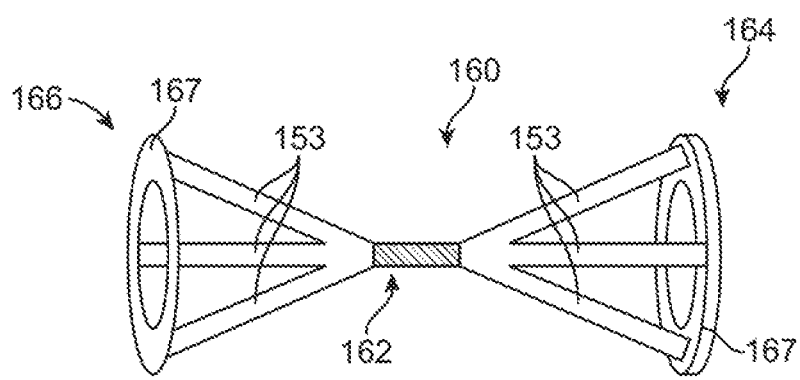

FIGS. 9A-9C illustrate alternative embodiments of the stimulation device illustrating additional embodiments of the body providing structure for gastric retention. In particular, stimulation device 140 of FIG. 9A includes a gastric O-ring 147 on proximal occlusion member 146. Stimulation device 150 of FIG. 9B includes a double funnel body wherein each of occlusion members 154 and 156 is configured as a funnel, thereby allowing food passage through the center of stimulation device 150. Finally, in FIG. 9C, stimulation device 160 is illustrated having a double O-ring configuration, in which an O-ring 167 is provided on each of occlusion members 164 and 166. Each of these embodiments utilizes a stimulation member 148, 158 and 168, such as an electrode and energy transmitter anywhere on the device, but in these illustrations, the stimulation member is shown on the pylorus-spanning element, i.e., bridging members 142, 152 and 162, respectively. In each of the O-ring embodiments, the occlusion members may be constructed from flexible supports, such as supports 143 and 153 that provide an expandable scaffold.

Figure 10A:
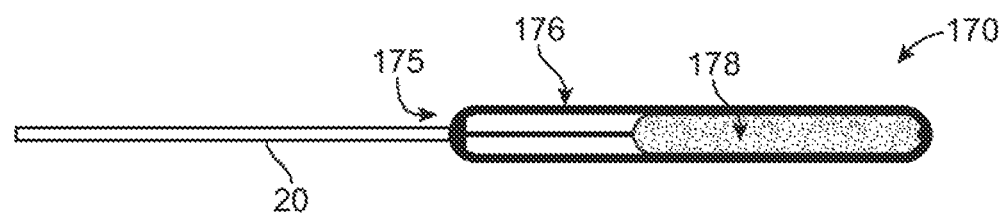
FIGS. 10A-10C are side views of various embodiments of a stimulation device.
Figure 10B:
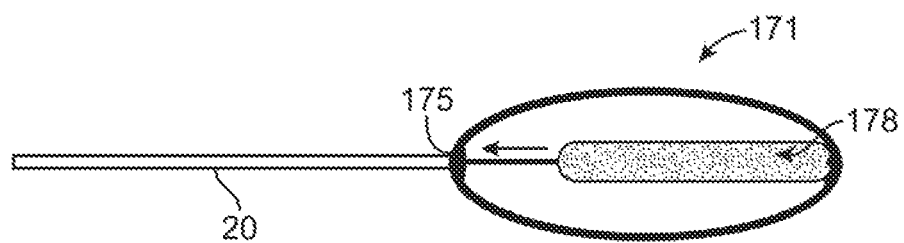
Figure 10C:
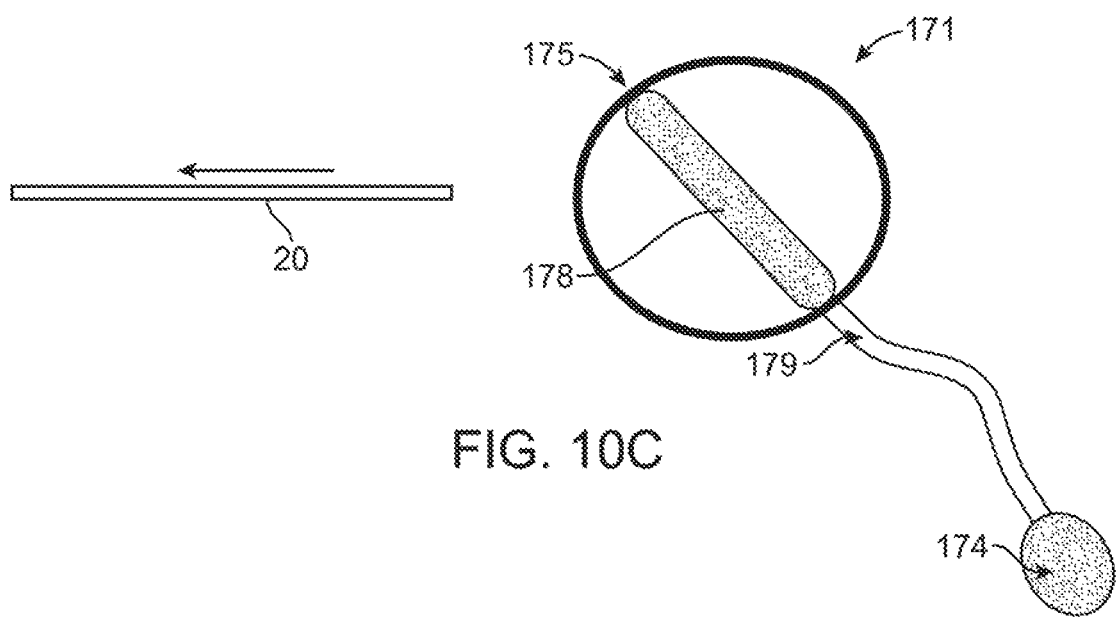

FIGS. 10A-10C depict another embodiment of a stimulation device 170 that includes a body 171 and stimulation member 178 that is encased within body 171. Stimulation device 170 may include a single expandable portion that forms body 171, as shown in FIGS. 10A and 10B, or optionally both distal and proximal members 174 and 176, as shown in FIG. 10C. In this embodiment, either shape memory or endoscopic manipulation may be used to expand the device after gastric insertion.

Preferably, in the present embodiment, body 171 is constructed from self-expanding cages, coils, lattices, frameworks or the like. In FIG. 10A, body 171 is constructed from an expanding scaffold, which may be coupled with a wall 173 of stimulation device 170 on its inner or outer surface, or the expanding scaffolding may be embedded in wall 173.

The expanding scaffolding may be composed of shape memory or super-elastic materials, such as Nitinol. The scaffold may be compressed into a delivery configuration and then either allowed to expand into the desired occlusive shape by self-expansion or expanded by supplying an activation energy, such as, electrical energy, heat, RF energy or the like. In another embodiment, the scaffold may be deployed by pulling the scaffold into an expanded configuration with a pulling device, and in such embodiments, the scaffold may have a catch mechanism or other locking feature to prevent it from collapsing to its original shape.

Locking features (not shown), such as a tether, may be included on body 171 to lock body 171 in the expanded configuration, shown in FIG. 10C. In the locking embodiment, endoscopic manipulation may be used to lock the device. Locking may be reversed or disengaged through snipping off a fiber, snaring of a ball or grasping using forceps after which the device may be firmly engaged using a snare, forceps or another endoscopic tool, for extraction.

Stimulation device 170 includes insertion port on a proximal end of body 171. Insertion port 175 provides a coupling mechanism for an insertion or extraction catheter 20 to be coupled to stimulation device 170 so that the device ma be manipulated.

FIG. 10C illustrates stimulation device 170 with an optional tether 179 and distal occlusion member 174. In this embodiment, during implantation, distal occlusion member 174 may pass into the intestine and hold the device against the pyloric valve for purposes of obstructing gastric outflow and maintaining electrical contact with the pyloric valve, stomach or intestine, similar to the previously described embodiments.

Figure 11A:
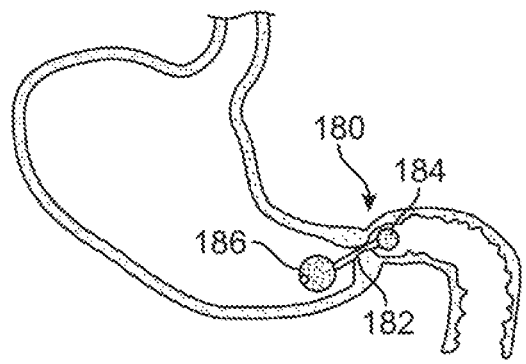
FIGS. 11A-11D are partial side views of another embodiment of a stimulation device.
Figure 11B:
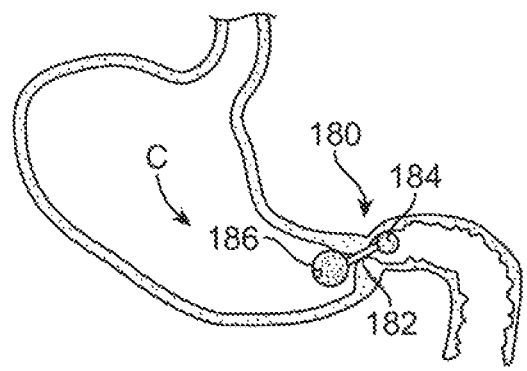
Figure 11C:
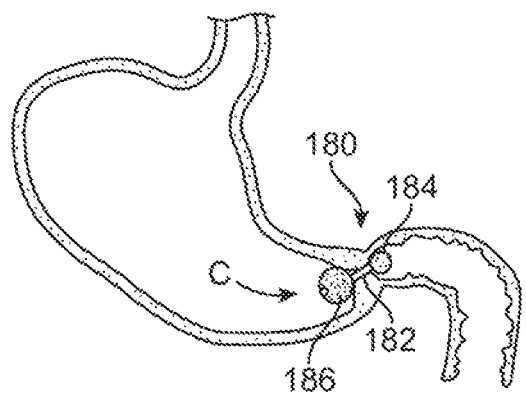
Figure 11D:
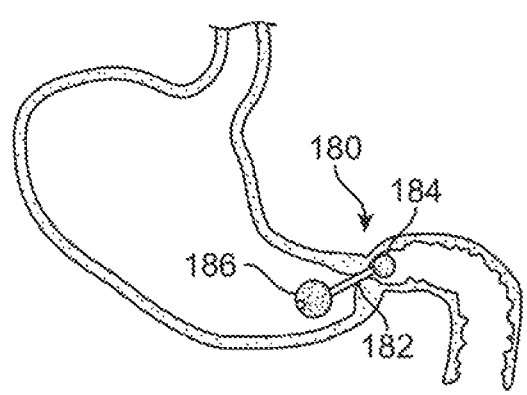

FIGS. 11A-11D illustrate stimulation device 180 capable of both reducing the rate of gastric emptying and ensuring a snug electrode contact to the gastrointestinal tract. For example, as shown in FIG. 11A, stimulation device 180 is implanted so that occlusion members 184 and 186 are disposed on either side of the pyloric valve and so that bridging member 182 is disposed within the pyloric valve. When the selected triggering condition is not present, bridging member 182 is elongated. After the triggering condition C is sensed, bridging member 182 begins to contract, as shown in FIG. 11B, and bridging member 182 continues to contract while the condition remains, as shown in FIG. 11C. It should be appreciated that bridging member 182 is selected so that it presents a desired minimum contracted length. After the triggering condition is removed, bridging member 182 expands, as shown in FIG. 11D.

Through the use of bridging member 182 that may decrease in length under selected conditions (i.e. once food is sensed through changes in pH, temp, pressure waves, force, etc. or upon receipt of an external signal) or according to a set timeline the proximal and distal bulbs may be drawn towards the pyloric valve. This action may provide either a more effective obstruction of the gastric outlet (and reduction in the rate of gastric emptying) and/or a more firm contact between stimulation member 188 and the gastric and intestinal surfaces. This action may increase the efficacy of stimulation device 180 with respect to energy transmission and, in the embodiment without electrical stimulation, will provide a more effective, focused reduction in the rate of gastric emptying.

In use, after stimulation device 180 no longer senses the selected condition or the correct amount of time has elapsed, the device may return to its original configuration with longer bridging member 182. Stimulation device 180 may also increase or decrease in other dimensions (i.e. the pylorus spanning element may increase in diameter, etc.) under selected conditions or at designated times.

In this and other embodiments, proximal occlusion member, bridging member and/or distal occlusion member may be adapted to change configurations while the device resides in the gastrointestinal tract. For example, in some embodiments, bridging member changes its length and/or its diameter. Such configuration changes may be triggered by receipt and processing of one or more signals by a receiver and processor of the device. For example, signals may be transmitted by an external device to the internal stimulation device using radiofrequency, electromagnetic, microwave or ultrasound signals. Alternatively, configuration changes may be triggered upon sensing of pH, temperature, bile content, nutrient content, fats, sugars, alcohol, opiates, drugs, analytes, electrolytes and/or hemoglobin by at least one sensor of the device.

Figure 12A:
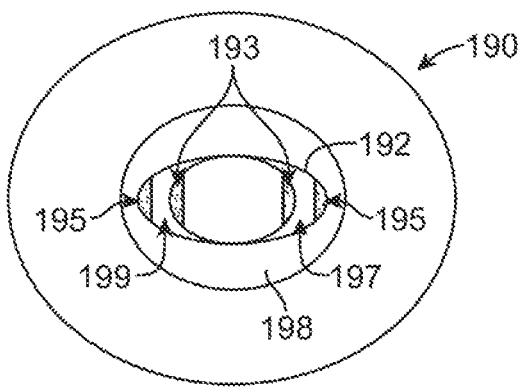
FIGS. 12A and 12B are cross-sectional views of a bridging member portion of an embodiment of a stimulation device.
Figure 12B:
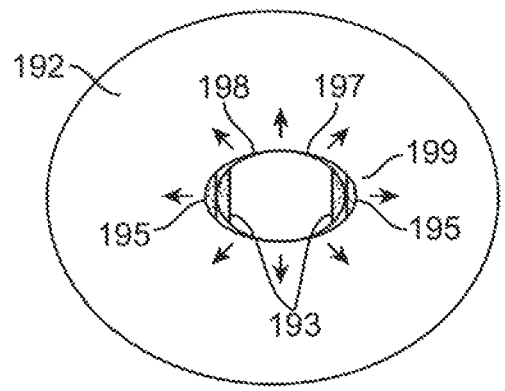

FIGS. 12A, 12B, 13A and 13B illustrate additional embodiments of the stimulation device whereby contraction of the pyloric valve around the bridging member triggers a switch to activate or deactivate stimulation of the stimulation device. Referring to FIGS. 12A and 12B, the contraction of the pyloric valve around bridging member 192 of stimulation device 190 triggers stimulation of adjacent tissues through stimulation member 198. In particular, bridging member 192 is constructed from generally concentric members 197 and 199. Electrodes 193 and 195 are disposed on members 197 and 199 and are oriented so that each electrode of member 197 is located adjacent an electrode included on member 199. Contraction of the pyloric valve places complimentary electrodes 193 and 195 in contact and that contact allows for the transmission of energy only when the pyloric valve is contracted and snug up against bridging member 192.

Figure 13A:
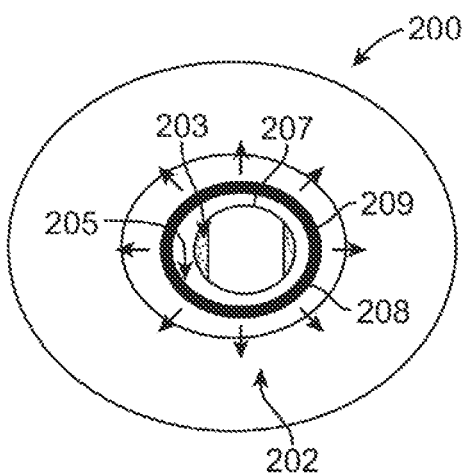
FIGS. 13A and 13B are cross-sectional views of a bridging member portion of another embodiment of a stimulation device.
Figure 13B:
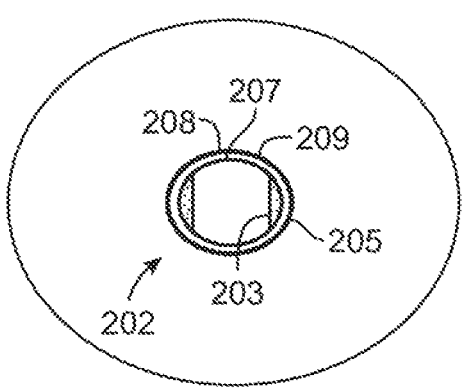

In FIGS. 13A and 13B, stimulation device 200 is illustrated. Stimulation device 200 is similar to stimulation device 190, however, it is configured so that contact between complementary electrodes 203 and 205 due to contraction of the pyloric valve and relative motion between members 207 and 209 causes the transmission of energy from stimulation member 208 to be interrupted. In this embodiment, members 197 and 199 have a generally round cross-sectional shape, unlike the elliptical shape of the members of device 190. Stimulation device 200 is activated when electrodes 203 and 205 lose contact as shown in FIG. 13A. When electrodes 203 and 205 are in contact, as shown in FIG. 13B, stimulation device 200 is deactivated to allow for pacing and/or energy transmission only when the pyloric valve is dilated. It should be appreciated that the shape of the flexible members of stimulation devices 190 and 200 is not limited to those shown in the illustrated embodiments.

These embodiments allow for the transmission of energy only when prescribed and result in better efficiencies. Combined with triggering of energy transmission only under with external or internally generated signals (i.e. sensors as mentioned above), this feature will allow for much longer battery life between charges. This feature also allows the device to be used for a variety of purposes other than weight reduction. For example, with the correct pacing strength and frequencies under the appropriate conditions (i.e. pyloric dilation, etc.), the device could be used to increase the rate of gastric emptying and may be used for severe gastroparesis and/or dyspepsia.

Figure 14A:
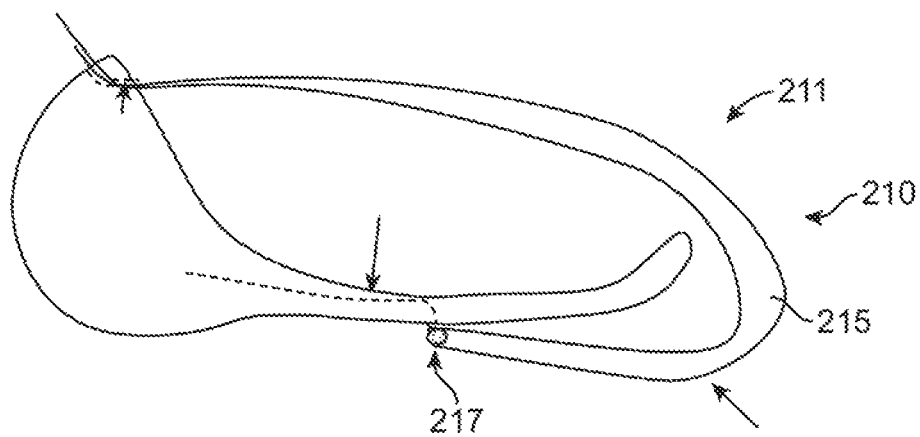
FIGS. 14A-14C are side views of another embodiment of a stimulation device.
Figure 14B:
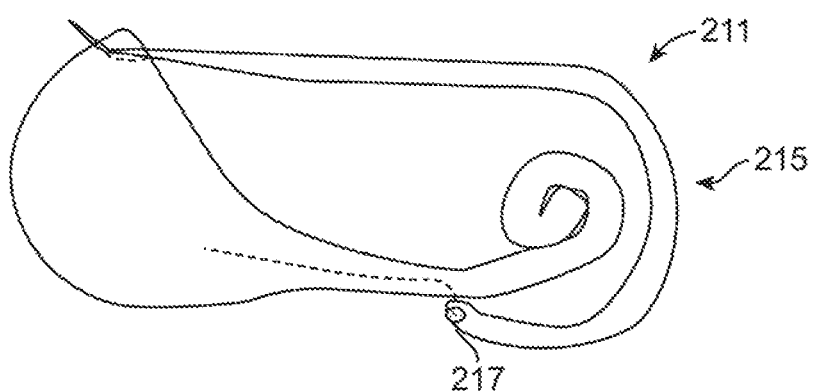
Figure 14C:
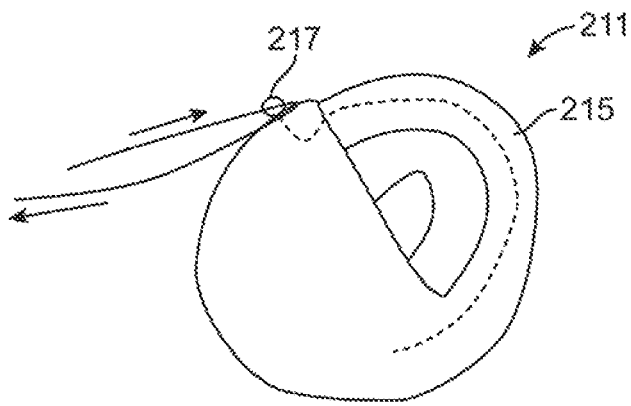

FIGS. 14A-14C illustrate another structure for body 211 of stimulation device 210 wherein the device may be extended for insertion and then rolled or folded once in the desired position within or adjacent the pyloric valve. In this embodiment, an elongate band 215 is in a contracted, delivery configuration when it is in an elongate state and it is in an expanded configuration when it is rolled or folded and locked in place with a locking feature. In particular the locking feature includes a locking button 217 which may be pulled through a locking lumen 219 included on band 215 once the desired configuration has been obtained.

If it is desired to contract stimulation device 210, button 217 may be simply removed endoscopically in order to unlock the device for extraction. In this embodiment, a stimulation member may be included on any onion of body 211.

According to various embodiments, any of a number of suitable energy delivery members, sensors, transmitters, receivers, processors and/or the like may be coupled with any of the devices described below. Furthermore, such energy delivery members, sensors and the like may be coupled with any suitable part of a device, such as a portion of a device adapted to reside in the stomach, another portion adapted to span the pyloric valve, a portion adapted to reside just beyond the pyloric valve in the duodenum, or some combination thereof.

Alternatively, any of the devices described herein could be altered to allow for anchoring in the duodenal bulb. As with the pyloric sphincter in the stomach, the duodenal bulb necks down to a smaller lumen creating an effective sphincter. Any of the above devices could be modified to provide for retention in the duodenal bulb without the need for excessively firm stenting or puncture of the intestinal wall. Through the use of this embodiment, the intestine could be effectively stimulated without the need for a gastric component. In addition, the device of the present invention could be used to anchor a gastrointestinal energy delivery device in any region of the gastrointestinal tract where there is a decrease in lumen diameter sufficient to maintain an interference fit. This includes the pharynx, the esophagus (upper, cardiac and lower sphincters), the pylorus, the duodenal bulb, the ileocecal valve, the rectum and any other region with sufficient change in diameter to anchor a stimulating device through an interference fit.

Another embodiment may incorporate slow-releasing therapeutic substances, such as drugs infused into the materials covering the device or materials incorporated into the device. These therapeutic substances, which may be any number of drugs, may slowly infuse into the patient by drug release into the intestinal tract or through contact with the patient. Alternatively, the devices may incorporate electrical stimulation technologies. For instance, electrical probes may extend from a surface of the device for insertion into the surrounding tissue or electrodes may be formed over a surface of the device.

Although these variations show specific shapes, these are merely intended to be illustrative of the various types of shapes that may be utilized and is not intended to be limiting. For instance, any shape, such as rectangles, squares, etc., which may function to occlude, or partially occlude, a gastric opening and prevent the device from falling therethrough may be utilized and are within the scope of this disclosure. Moreover, various combinations of the different shapes as occlusion members or contact electrodes on a single device may also be utilized, such as a device having a distal occlusion member in the shape of a sphere and a proximal occlusion member in the shape of a cone.

As was described above, in some embodiments a stimulation device may be delivered via an elongate catheter device, such as an orogastric or nasogastric tube, passed through the patient's esophagus into the stomach. That same delivery catheter device or a separate device may also be adapted for use in modifying, adjusting and/or recharging the stimulation device once it is in place in the stomach. This would allow a device to be modified without removing the device or requiring device replacement.

Figure 15A:
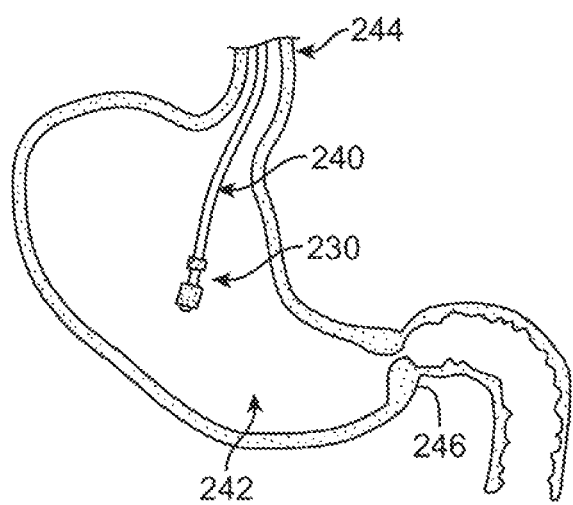
FIGS. 15A-15C are side views illustrating steps of a method of inserting a stimulation device.
Figure 15B:
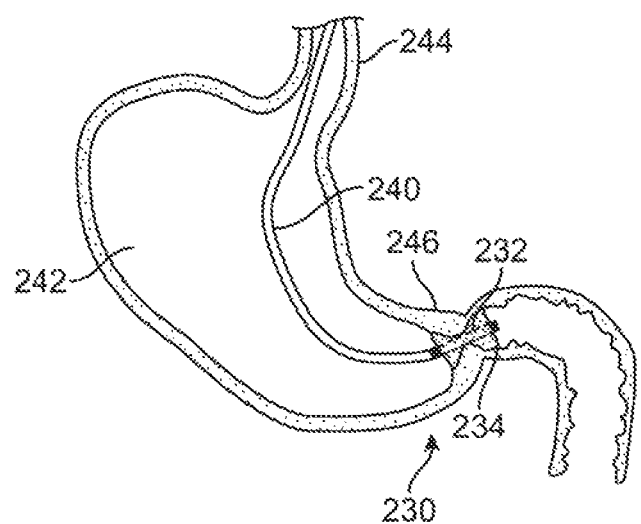
Figure 15C:
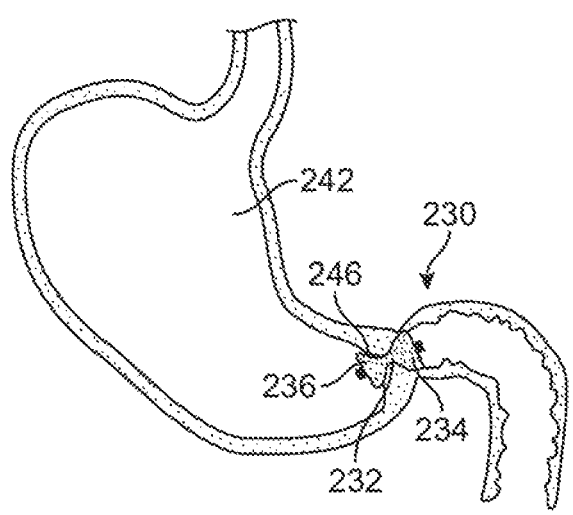

Referring to FIGS. 15A-15C a method of transpyloric insertion of a stimulation device is illustrated. The device is configured to maintain constant contact while shifting with the gastric wall, pylorus or duodenum without requiring firm fixation. This allows a firm contact for a stimulation member of the device but will avoid the difficulties of firmly anchoring any device to the gastric wall.

As shown in FIG. 15A stimulation device 230 is advanced into a patient's stomach 242 via the esophagus 244 using a catheter 240 or other elongate implantation device. Stimulation device 230 is advanced until the distal end of the device is located distal of the pyloric valve 246. Distal occlusion member 234 is inflated or expanded and stimulation device 230 may then be pulled proximally against the pyloric valve 246. Next, proximal occlusive member 236 may be inflated or expanded. With both occlusion members 234, 236 inflated or expanded, bridging member 232 connecting the two spans the pyloric valve 246 and a stimulation member is located at a desired position adjacent a target tissue, as shown in FIG. 15B. After occlusion members 234 and 236 are inflated or expanded, catheter 240 is detached from stimulation device 230 and removed, thereby leaving stimulation device 230, as shown in FIG. 15C.

Figure 16A:
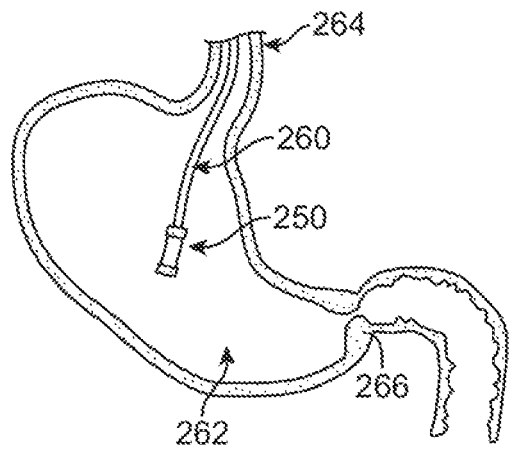
FIGS. 16A-16C are side views illustrating steps of a method of inserting a stimulation device.
Figure 16B:
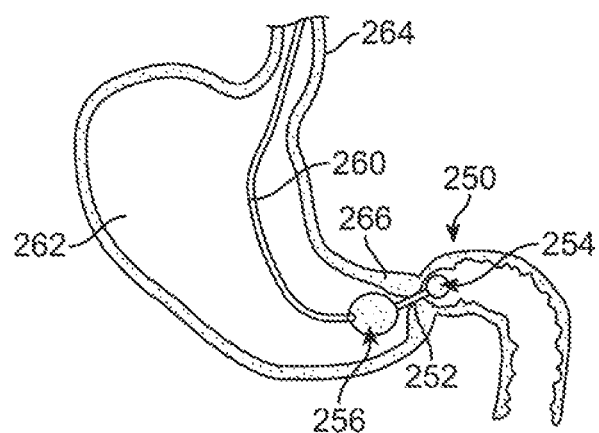
Figure 16C:
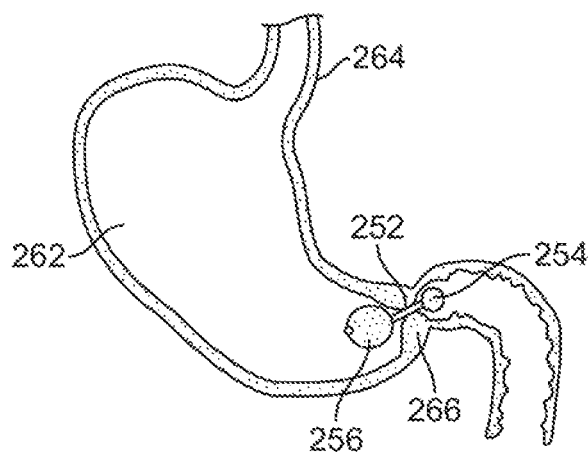

In FIGS. 16A-16C a method of transpyloric insertion of a stimulation device is illustrated with another embodiment of the stimulation device. As shown in FIG. 16A stimulation device 250 is advanced into a patient's stomach 262 via the esophagus 264 using a catheter 260 or other elongate implantation device. Stimulation device 250 is advanced until the distal end of the device is located distal of the pyloric valve 266. Distal occlusion member 254 is inflated or expanded and stimulation device 250 may then be pulled proximally against the pyloric valve 266. Next, proximal occlusive member 256 may be inflated or expanded. With both occlusion members 254, 256 inflated or expanded, bridging member 252 connecting the two spans the pyloric valve 266 and a stimulation member is located at a desired position adjacent a target tissue, as shown in FIG. 16B. After occlusion members 254 and 256 are inflated or expanded, catheter 260 is detached from stimulation device 250 and removed, thereby leaving stimulation device 250, as shown in FIG. 16C.

Figure 17A:
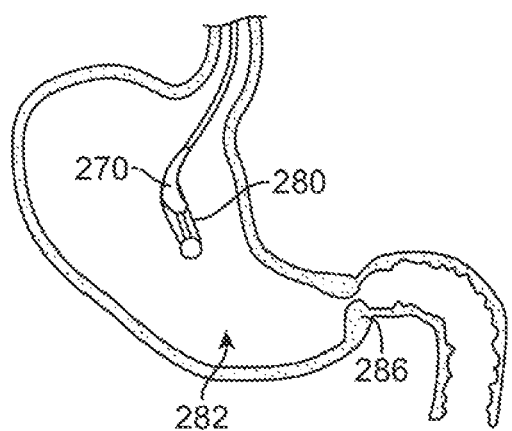
FIGS. 17A-17C are side views illustrating steps of a method of inserting a stimulation device.
Figure 17B:
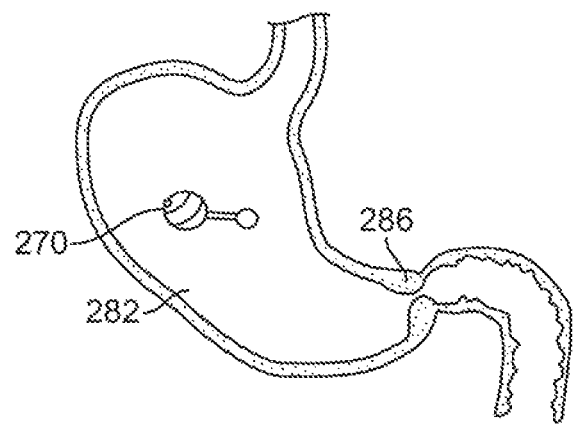
Figure 17C:
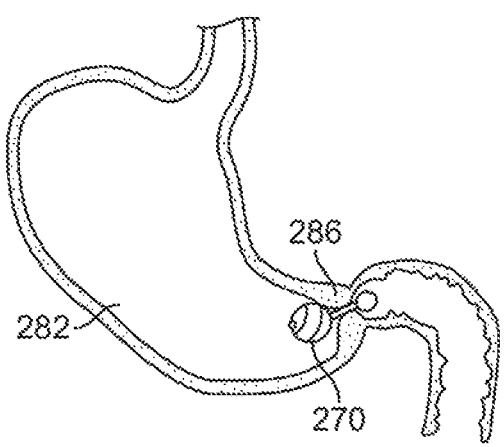

Referring to FIGS. 17A-17C another method of gastric insertion of stimulation device 270 is illustrated. In FIG. 17A, stimulation device 270 is compressed within a delivery pod 280. After delivery pod 280 is located within the stomach 282, stimulation device 270 is, either due to shape-memory properties of the material itself or due to endoscopic manipulation. As shown, at least proximal occlusion member 276 of stimulation device 270 has a spiral structure in which the device spirals into a sphere or other shape, which is not able to be passed by the pyloric valve 286. As shown in FIG. 17B, after release of stimulation device 270 from delivery pod 280, stimulation device migrates or is advanced through the stomach 282. Stimulation device 270 naturally migrates through the stomach 282 or is manipulated until it is located and oriented as shown in FIG. 17C.

Figure 18A:
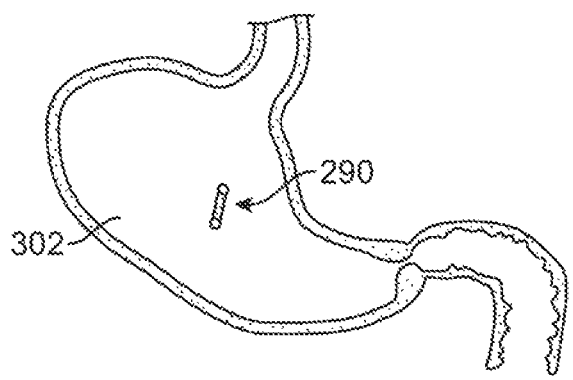
FIGS. 18A-18C are side views illustrating steps of a method of inserting a stimulation device.
Figure 18B:
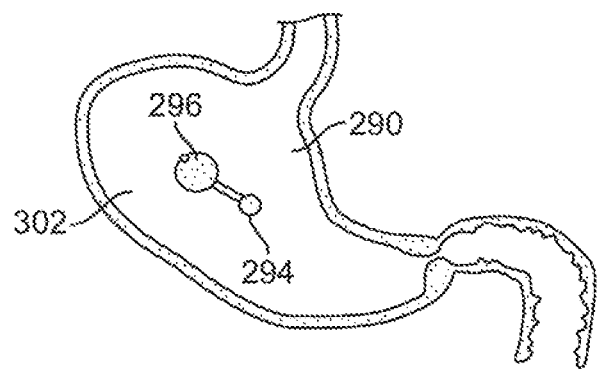
Figure 18C:
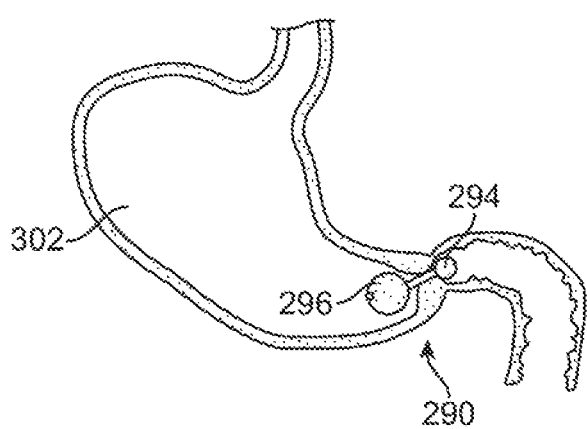

Referring to FIGS. 18A-18C another method of implantation of a stimulation device is illustrated. In the illustrated method, an ingestible embodiment, stimulation device 290, is utilized. In this variation, the device is packaged into a large pill-sized container and expands upon reaching the stomach. The device then migrates until it is located across the pylorus due to the passage of distal occlusion member 294.

As stimulation device 290 enters the stomach 302, as shown in FIG. 18A, both the proximal and distal occlusion members 296 and 294, respectively, may be configured to inflate upon erosion of acid-sensitive coatings over an inflation port of device 290, as shown in FIGS. 18B and 18C. After inflation or expansion, the distal occlusion member 294 will eventually be passed due to its smaller size (approximately the diameter of the dilated pyloric valve 5-15 mm) while the proximal occlusion member 296 will remain in the stomach 302 due to its larger size, e.g., 15 mm or greater in diameter and up to 60 mm in diameter due to physiologic limitations in the pyloric region of the stomach, as shown in FIG. 18C. Thus, distal occlusion member 294 may be designed to be small enough to be passed through the pyloric valve while the proximal occlusion member 296 may be designed to be retained in the stomach 302. The device, in this embodiment, may be permanent, and require removal, or degradable and pass on its own.

A number of different alternatives and variations may be employed in self-expanding gastric stimulation devices and methods. In some embodiments, a device may be folded, compressed or otherwise formed into a smaller configuration for swallowing by a patient, without using a biodegradable coating. Upon passing through the esophagus into the stomach, the folded device may unfold due to one or more shape-memory Nitinol support rings or other self-expanding support members. In any swallowing embodiment, a stimulation device may also include a tether that extends from the device, back through the esophagus to the patient's mouth. Such a tether may be used for retaining the obstructing device in the stomach until it expands, and/or retrieving the obstructing device if it does not deploy as desired in the patient's stomach. The tether may be swallowed to dissolve in the stomach. In other embodiments, a swallowed device may contact the pyloric valve but not include a bridging member for spanning the valve. Other variations are contemplated within the scope of the invention, according to various embodiments.

Figure 19A:
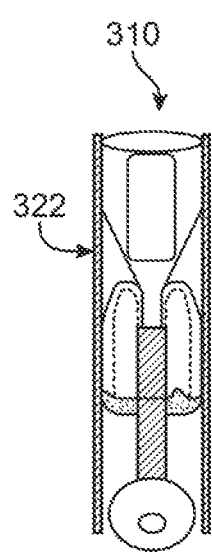
FIGS. 19A-19C are side views illustrating steps of a method of inserting a stimulation device.
Figure 19B:
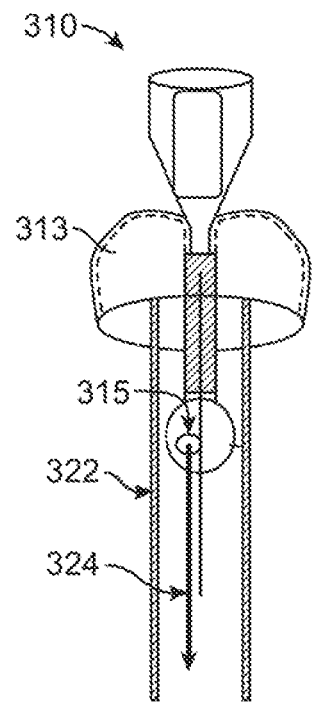
Figure 19C:
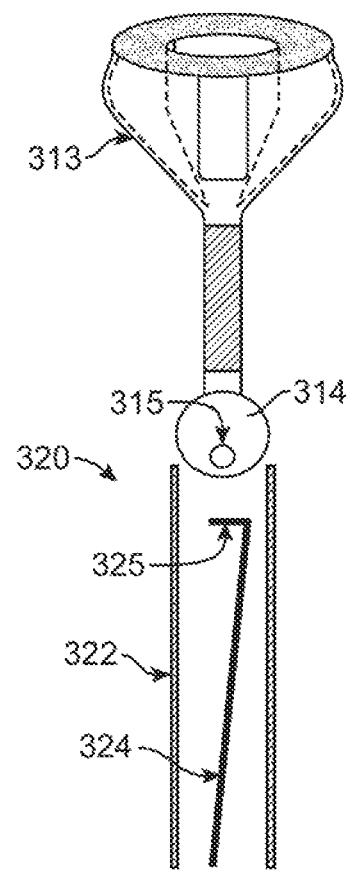

Referring to FIGS. 19A-19C a method for delivering and deploying a stimulation device 310 including an invertible shell will be described. In FIG. 19A, stimulation device 310 is housed within the lumen of a delivery tube 322 of a delivery device 320 or catheter in its collapsed configuration. In FIG. 19B, stimulation device 310 has been advanced partially out of delivery tube 322, allowing shell 313 to at least partially expand. A delivery member 324 may include a hook feature 325 which is hooked through hole 315 on distal occlusion member 314 then be used to pull back on stimulation device 310, such that the shell 313 overlaps the distal end of delivery tube 322. The distal end of delivery tube 322 is then used to apply force to shell 313, causing it to invert into its expanded state, as shown in FIG. 19C.

After shell 313 is moved to its expanded configuration, it is designed to stay in that configuration, thus providing the pyloric valve contacting and device retention functions described above. In an embodiment, delivery tube 322 may include an expandable balloon (not shown) at or near its distal end. The balloon may be doughnut-shaped to inflate circumferentially, or may have any other suitable shape. The balloon may be inflated and serve as a stop against which stimulation device 310 may be pulled. Alternatively, the balloon may be inflated under or within stimulation device 310 to invert shell 313 as the balloon inflates.

In other embodiments, the device may be delivered and/or deployed using any other suitable method. For example, in one embodiment shell 313 may "self-invert" from its constrained/collapsed state to its expanded state without using an actuator or delivery member. Self-inverting may be achieved by shape-memory or spring-loaded materials or the like, or by a shell geometry that creates a bias in the stiffness of the device.

Figure 20A:
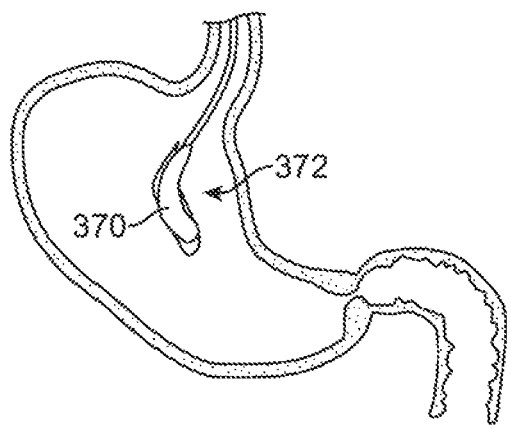
FIGS. 20A-20C are side views illustrating steps of a method of inserting a stimulation device.
Figure 20B:
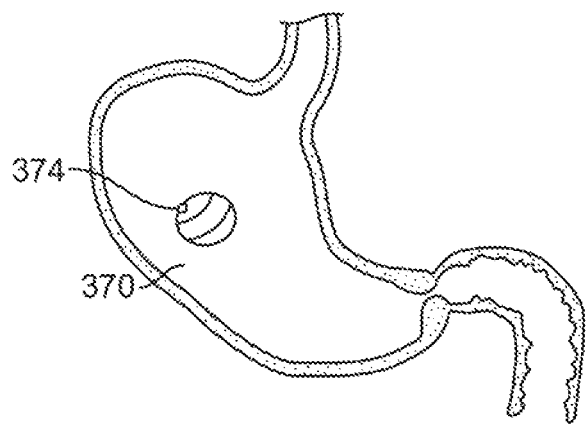
Figure 20C:
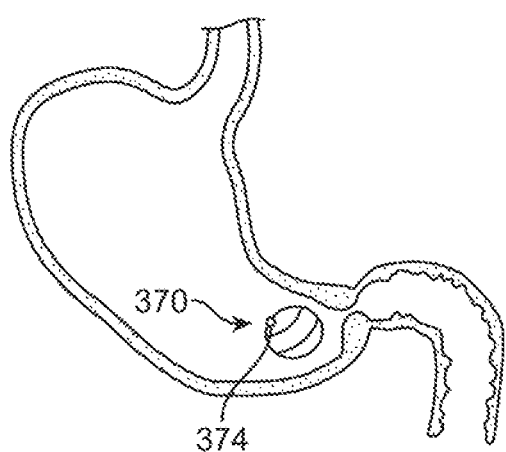

FIGS. 20A-20C illustrate a method for delivering and deploying an embodiment of the stimulation device that includes a single expandable portion for the body. In this embodiment, the stimulation device is fully intragastric and may be deployed using a pod system 372, as shown. Stimulation device 370 is deployed from pod system 372 into the stomach, or is swallowed, and the device migrates into position. In this case, a spiral design is shown in which the device spirals into a sphere or other shape, which is not able to be passed by the pylorus. A locking member 374 may also be included which allows stimulation device to be controlled for implantation or removal.

Figure 21A:
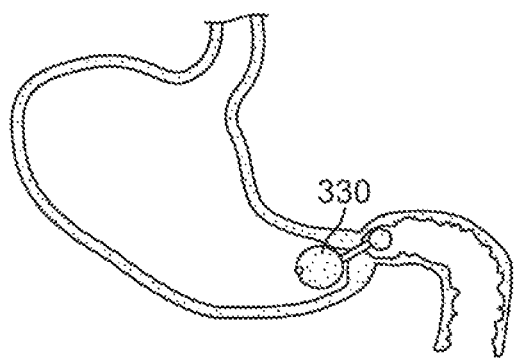
FIGS. 21A-21D are side views illustrating steps of a method of removing a stimulation device.
Figure 21B:
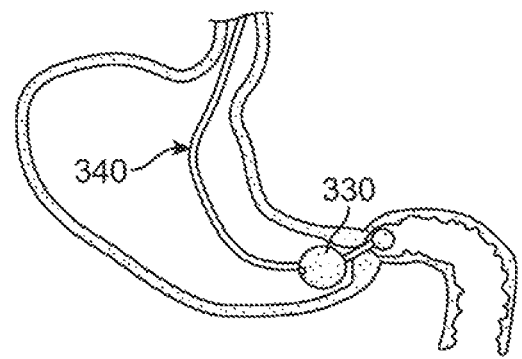
Figure 21C:
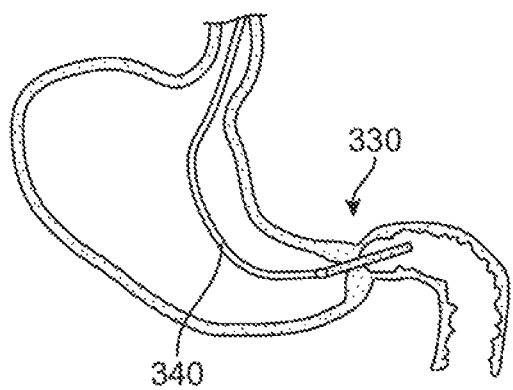
Figure 21D:
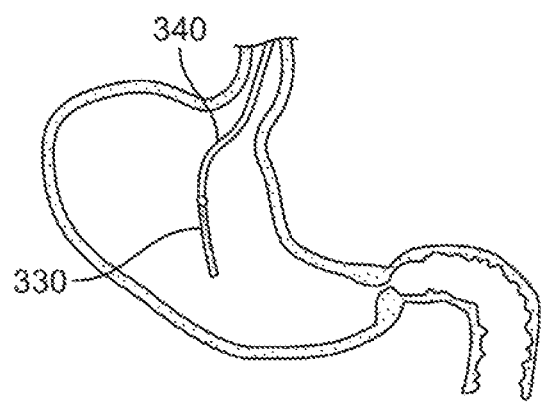

FIGS. 21A-120 illustrate a method of the removal of an inflatable embodiment of the stimulation device using suction or endoscopic manipulation. Stimulation device 330 can either be engaged endoscopically or engaged via a self-finding mechanism, i.e. magnetic attraction. Stimulation device 330 is shown in FIG. 21A between the stomach and the duodenum. As seen in FIG. 21B, a magnetic tipped suction catheter or endoscope 340 is introduced and stimulation device 330 may be deflated and removed, as shown in FIGS. 21C and 21D.

In contacting an inflation port of stimulation device with catheter 340, the tip of catheter 340 may be configured with an electrical contact as an aid in determining whether catheter 340 has properly contacted the inflation port. Alternatively, stimulation device 330 may be removed through endoscopy or it may be designed to degrade over time and eventually be passed through the intestines.

In other embodiments, a gastric stimulation device may be removed by deflating, collapsing or elongating the device and removing it through a lumen of a catheter device. In one embodiment, the device may be cut into small pieces and removed through a catheter lumen. In yet another embodiment, the device may dissolve over time and pass harmlessly through the pyloric valve and the digestive system. Any number of suitable alternatives for removal or passage of the device are possible in various embodiments.

Figure 22A:
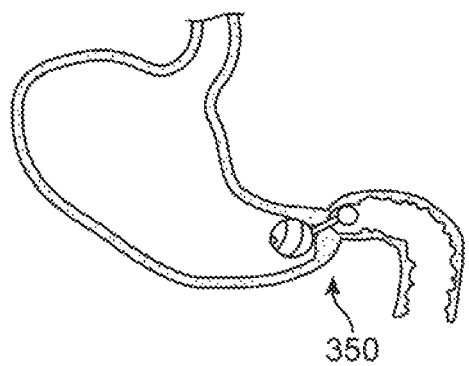
FIGS. 22A-22C are side views illustrating steps of a method of removing a stimulation device.
Figure 22B:
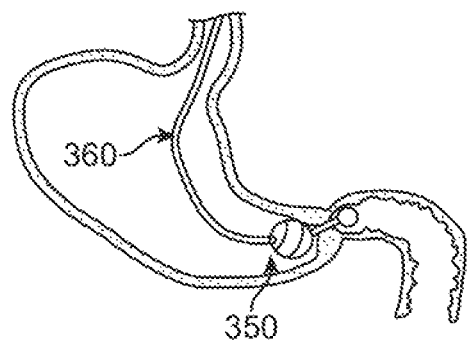
Figure 22C:
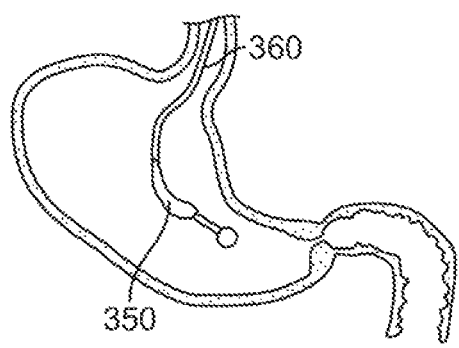
Figure 23A:
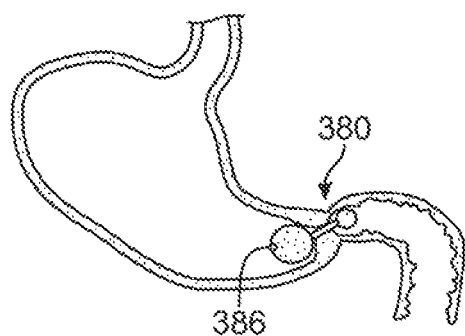
FIGS. 23A-23D are side views illustrating steps of a method of modifying a stimulation device.
Figure 23B:
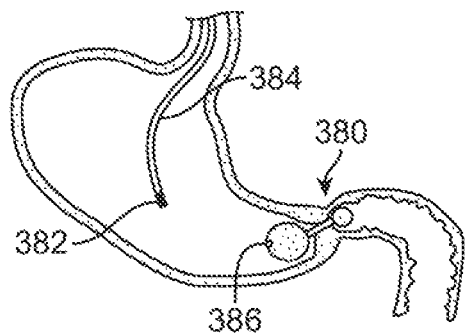
Figure 23C:
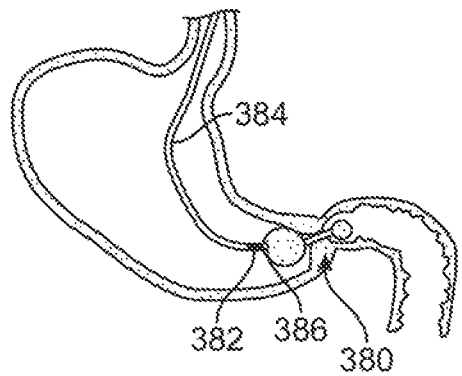
Figure 23D:
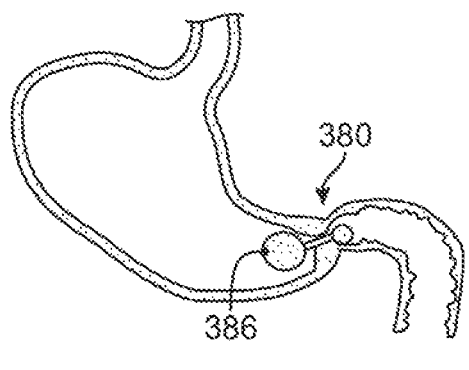

Another method of removal of a shape-memory embodiment of the stimulation device is illustrated in FIGS. 22A-22C. Stimulation device 350 is removed with a catheter 360 using suction or endoscopic manipulation. Stimulation device can either be engaged endoscopically or engaged via a self-finding mechanism, i.e. magnetic attraction, and is designed to be retracted with simple traction. Alternatively, and preferably, the stimulation device may require a quick endoscopic maneuver to release a locking mechanism prior to device collapse removal.

FIGS. 23A-23D illustrate a charging, refilling or programming of a stimulation device. In this embodiment, the charger, refiner or programmer 382 is attached to catheter 384 which may be inserted orally or nasally into the gastric space with or without imaging capabilities. In the instance that imaging capabilities are employed, catheter 384 is directed to a charging, refilling or programming port 386 of stimulation device 380 and the device is engaged and altered. Subsequently, catheter 384 is removed: Alternatively, a magnetically-tipped catheter could be used to engage a conducting metal ring at the site of manipulation and the catheter may be inserted blindly and register (i.e. through a noise, a light, etc.) once the catheter has engaged stimulation device 380. The device may then be charged, refilled, programmed, repositioned or even removed once it has been engaged. Charging, programming or interrogating the unit may also be accomplished using an external signal generator/receiver (not illustrated).

It should be appreciated that any method may be used to implant, remove or otherwise manipulate the stimulation device. For example, the methods may be minimally invasive, such as those described above. Alternatively, the methods may be invasive.

Although the above is a complete and accurate description of the invention, any of a number of variations, additions and the like may be made to the embodiments described without departing from the scope of the invention. For example, devices and methods described above may be used to treat any suitable condition or perform any suitable function within the gastrointestinal tract. Therefore, the foregoing description is provided primarily for exemplary purposes and should not be interpreted to limit the scope of the invention as it is defined in the following claims.

I claim:

1. An intragastric weight-loss device, comprising:
 a first occlusion member comprising a spiral structure, wherein the spiral structure is configured to form into a bulbous shape when the first occlusion member is delivered into the stomach;

a bridging member extending from the first occlusion member; and a second occlusion member coupled to a distal end of the bridging member, wherein the first occlusion member is configured to intermittently block the pyloric valve of a patient after deployment of at least the first occlusion member of the intragastric weight-loss device such that passage of food through the pyloric valve is slowed.

2. The device of claim 1, wherein the bulbous shape of the spiral structure is a substantially spherical shape.

3. The device of claim 1, wherein the first occlusion member comprises a compressed delivery configuration and an expanded deployed configuration.

4. The device of claim 3, wherein an outer dimension of the first occlusion member in the expanded deployed configuration is between about 50 mm and about 60 mm.

5. The device of claim 3, wherein the first occlusion member is expandable from the compressed delivery configuration into the expanded deployed configuration when within the stomach.

6. The device of claim 1, wherein a cross-sectional width of the bridging member is about 5 mm.

7. The device of claim 1, wherein the second occlusion member is sized to pass through the pyloric valve through natural peristalsis.

8. The device of claim 1, wherein the second occlusion member is substantially spherical in shape.

9. The device of claim 8, wherein a diameter of the second occlusion member is smaller than an outer dimension of the first occlusion member in an expanded deployed configuration but larger than a cross-sectional width of the bridging member.

10. The device of claim 1, further comprising a therapeutic substance configured to be released from the device.

11. The device of claim 10, wherein the therapeutic substance is a drug.

12. The device of claim 1, wherein a length of the bridging member is sized to span the length of the pyloric valve.

13. The device of claim 1, wherein the first occlusion member further comprises a locking member configured to control delivery or removal of the device.

14. The device of claim 1, wherein the first occlusion member comprises a shape-memory material.

* * * * *